(12) United States Patent
Hawkins et al.

(10) Patent No.: US 7,118,878 B1
(45) Date of Patent: Oct. 10, 2006

(54) METHOD FOR INCREASING LUMINESCENCE ASSAY SENSITIVITY

(75) Inventors: Erika Hawkins, Madison, WI (US); John M. Centanni, Madison, WI (US); Jacqueline Sankbeil, Edgerton, WI (US); Keith V. Wood, Madison, WI (US)

(73) Assignee: Promega Corporation, Madison, WI (US)

( * ) Notice: Subject to any disclaimer, the term of this patent is extended or adjusted under 35 U.S.C. 154(b) by 1035 days.

(21) Appl. No.: 09/590,884

(22) Filed: Jun. 9, 2000

(51) Int. Cl.
*C12Q 1/66* (2006.01)
(52) U.S. Cl. .......................... 435/8; 435/968
(58) Field of Classification Search .................... 435/8, 435/4, 39, 968, 975; 422/52, 82.08; 436/164, 436/172
See application file for complete search history.

(56) References Cited

U.S. PATENT DOCUMENTS

| | | | |
|---|---|---|---|
| 4,235,961 A | | 11/1980 | Lundin |
| 4,246,340 A | | 1/1981 | Lundin et al. |
| 4,390,274 A | | 6/1983 | Berthold et al. |
| 4,650,770 A | * | 3/1987 | Liu et al. .................... 436/523 |
| 5,106,732 A | * | 4/1992 | Kondo et al. |
| 5,618,682 A | | 4/1997 | Scheirer |
| 5,629,168 A | * | 5/1997 | Kricka |
| 5,744,320 A | * | 4/1998 | Sherf et al. ..................... 435/8 |
| 5,795,729 A | * | 8/1998 | Lee ............................. 435/24 |
| 5,814,471 A | * | 9/1998 | Wood |
| 6,200,762 B1 | | 3/2001 | Zlokarnik et al. |
| 6,221,612 B1 | * | 4/2001 | Knapp et al. ................. 435/7.1 |
| 6,416,960 B1 | * | 7/2002 | Bryan ....................... 435/7.23 |
| 6,602,657 B1 | | 8/2003 | Bronstein et al. |
| 6,602,658 B1 | | 8/2003 | Bronstein et al. |
| 6,867,005 B1 | * | 3/2005 | Keys et al. ................... 435/7.1 |
| 2001/0006820 A1 | | 7/2001 | Knapp et al. |
| 2004/0096924 A1 | | 5/2004 | Hawkins et al. |
| 2004/0224377 A1 | | 11/2004 | Hawkins et al. |

FOREIGN PATENT DOCUMENTS

| | | |
|---|---|---|
| EP | 0 054 675 | 6/1982 |
| EP | 0 247 796 | 12/1987 |
| EP | 0 342 024 | 11/1989 |
| EP | 0 610 937 | 8/1994 |
| EP | 1 081 495 | 3/2001 |
| JP | 07-67696 | 3/1995 |
| WO | WO 92/04468 | 3/1992 |

OTHER PUBLICATIONS

Derwent abstract of JP 07067696A (Acc No 1995-143877). Reducing background luminescence in the detection of haem and peroxidase (1995).*

Armstrong et al., "Selectivity of Crown Ether (and Related) Ionophores for Small Metal Cations". Presented at the Spring, 2000 CONFCHEM, an on-line conference, Apr. 3-May 5, 2000.

Blaise et al., "A bacterial toxicity assay performed with microplates, microluminometry and Microtox reagent", *BioTechniques*, 16(5), 932-937 (1994).

Branchini et al., "Naphtyl- and Quinolylluciferin: Green and Red Light Emitting Firefly Luciferin Analogues", *Photochemistry and Photobiology*, 49(5), 689-695 (1989).

Bronstein et al., "Chemiluminescent and bioluminescent reporter gene assays", *Analytical Biochemistry*, 219(2), 169-181 (1994).

Bronstein et al., "Novel Chemiluminescent Adamantyl 1,2-Dioxetane Enzyme Substrates", In: Bioluminescence & Chemiluminescence: Current Status, Chichester ; New York : Wiley, eds. PE Stanley and LJ Kricka, Proceedings of the VIth International Symposium on Bioluminescence and Chemiluminescence, Cambridge, Sep. 1990, 73-82 (1991).

DeLuca et al., "Role of Sulfhydryl Groups in Firefly Luciferase", *Biochemistry*, 3, 935-939 (1964).

DeLuca et al., "The Hydrolase Properties of Firefly Luciferase", *Biochemical and Biophysical Research Communications*, 18, 836-842 (1965).

DeLuca et al., "The Role of 1,$N^6$-Ethenoadenosine Triphosphate and 1, $N^6$- Ethenoadenosine Monophosphate in Firefly Luminescence", *PNAS 70*, 1664-1666 (1973).

Denburg et al., "Anion inhibition of firefly luciferase", *Archives of Biochemistry & Biophysics*, 141, 668-675 (1970).

Denburg et al., "Substrate-binding properties of firefly luciferase. I. Luciferin-binding site.", *Archives of Biochemistry & Biophysics*, 134, 381-394 (1969).

Ford et al., "Enhancement of Firefly Luciferase Activity by Cytidine Nucleotides", *Analytical Biochemistry*, 204, 283-291 (1992).

Hastings, "Biological Diversity, Chemical Mechanisms, and the Evolutionary Origins of Bioluminescent Systems", *Journal of Molecular Evolution*, 19, 309-321 (1983).

(Continued)

Primary Examiner—Ralph Gitomer
(74) Attorney, Agent, or Firm—Schwegman, Lundberg, Woessner and Kluth P.A.

(57) ABSTRACT

The invention provides kits and methods for increasing the sensitivity of a bio-luminescent assay, which employ an organic compound that, for instance, reduces luminescence that is not dependent on the presence of an analyte by at least about 10 fold and reduces luminescence that is dependent on the presence of an analyte by less than about 7 fold, reduces luminescence generated by luminogenic molecules not bound to an enzyme by at least about 10 fold and reduces the luminescence generated by luminogenic molecules bound to an enzyme by less than about 7 fold, or reduces autoluminescence by at least about 10 fold and reduces luminescence that is dependent on the presence of an analyte by less than about 7 fold.

83 Claims, 4 Drawing Sheets

OTHER PUBLICATIONS

Kobatake et al., "Bioluminescent immunoassay with a protein A-luciferase fusion protein", *Analytical Biochemistry, 208(2)*, 300-305 (1993).

Leckie et al., "Normalization of GUS by luciferase activity from the same cell extract reduces transformation variability.", *Biotechniques, 17*, 52-53, 56-57 (1994).

Matthews, "Purification and properties of *Renilla reniformis* luciferase.", *Biochemistry, 16(1)*, 85-91 (1977).

McElroy et al., "Function of Adenosine Triphosphate in the Activation of Luciferin", *Archives of Biochemistry and Biophysics, 64*, 257-271 (1956).

McElroy et al., "Mechanisms of Bioluminescent Reactions", *In: A Symposium on Light and Life*, Edited by W. D. McElroy and B. Glass, John Hopkins Press, 219-257 (1961).

Moyer et al., "Nucleoside Triphosphate Specificity of Firefly Luciferase", *Analytical Biochemistry, 131*, 187-189 (1983).

Rhodes et al., "The Synthesis and Function of Luciferyl-adenylate and Oxyluciferyl-adenylate", *J. Biol. Chem., 233*, 1528-1537 (1958).

Rosendahl et al., "Dimensional Probing of the ATP Binding Site on Firefly Luciferase", *Photochemistry and Photobiology, 35*, 857-861 (1982).

Schaap et al., "Chemiluminescent substrates for alkaline phosphatase: application to ultrasensitive enzyme-linked immunoassays and DNA probes.", *Clinical Chemistry, 35*, 1863-1864 (1989).

Schram, "Evolution of Bioluminescent ATP Assays", *In: Bioluminescence and chemiluminescence : current status*, Chichester ; New York : Wiley, eds. P E Stanley; Larry J Kricka, Proceedings of the VIth International Symposium on Bioluminescence and Chemiluminescence, Cambridge, Sep. 1990, 407-412 (1991).

Seliger et al., "The Colors of Firefly Bioluminescence: Enzyme Configuration and Species Specificity", *PNAS, 52*, 75-80 (1964).

Thompson et al., "Modulation of firefly luciferase stability and impact on studies of gene regulation.", *Gene, 103*, 171-177 (1991).

Thorpe et al., "Enhanced chemiluminescent reactions catalyzed by horseradish peroxidase", *Methods in Enzymology, 133*, 331-353 (1986).

Ward, "Chemi-and Bioluminescence (ed. John Burr) Marcel Dekker, Inc., New York", *New York: M. Dekker*, 321-358 (1985).

Wood, "Marker proteins for gene expression", *Current Opinion in Biotechnology, 6*, 50-58 (1995).

Wood et al., "Recent advances and prospects for use of beetle luciferases as genetic reporters", In: Biolouminescence & Chemiluminescence: Current Status, Chichester ; New York : Wiley, eds. Stanley, PE and Kricka, J, Proceedings of the VIth International Symposium on Bioluminescence and Chemiluminescence, Cambridge, Sep. 1990, 543-46 (1991).

\* cited by examiner

Beetle Luciferin　　　　　　　　　　　　　Oxyluciferin

Coelenterazine　　　　　　　　　　Coelenteramide

Coelenterazine                dioxetane

Light + Coelenteramide

METHOD FOR INCREASING LUMINESCENCE ASSAY SENSITIVITY

FIELD OF THE INVENTION

The present invention relates generally to the fields of cell biology and molecular biology. In particular, this invention relates to methods, compositions and kits for increasing the sensitivity of a luminescence assay measurement.

BACKGROUND OF THE INVENTION

Reporter molecules are routinely used to monitor molecular events in the fields of biology, biochemistry, immunology, cell biology and molecular biology. For example, reporter molecules are employed in assays where the levels of the reporter molecule are due to transcription from a specific promoter linked to the reporter molecule. These assays can be used to study eukaryotic gene expression, receptor activity, transcription factors, intracellular signaling, mRNA processing, protein folding, and the like. Reporter molecules that are typically used in such assays include radioactive isotopes, fluorescent agents, enzymes, and luminescent agents. See for example, Akhavan-Tafti, et al, in: Bioluminescence and Chemiluminescence. Fundamentals and Applied Aspects. Proceedings of the 8th International Symposium on Bioluminescence and Chemiluminescence. Cambridge, September 1994. Eds. Campbel, Kricka, Stanley. John Wiley and Sons 1994.

Two luminescent enzymes that are particularly useful in assay systems are firefly luciferase and *Renilla reniformis* luciferase. The substrates for these luciferases and the reaction products they produce are shown in FIGS. 1 and 2. The quantity of light (i.e. the number of photons) produced in the reaction, can be measured and used to calculate the concentration of luminescent enzyme in the reaction.

Firefly luciferase is a 61 kDa monomeric protein that does not require post-translational processing for enzymatic activity. Thus, it functions as a genetic reporter immediately upon translation. Photon emission is achieved through oxidation of beetle luciferin in a reaction that requires ATP, $Mg^{2+}$ and $O_2$ (FIG. 1).

*Renilla* luciferase is a 36 kDa monomeric protein that is composed of 3% carbohydrate when purified from its natural source, *Renilla reniformis*. Like firefly luciferase, post-translational modification of *Renilla* luciferase is not required for its activity, and it functions as a genetic reporter immediately following translation. The luminescent reaction catalyzed by *Renilla* luciferase utilizes $O_2$ and coelenterate-luciferin, also called coelenterazine (FIG. 2).

Luminescent reactions can be used to detect very small quantities of a particular analyte, the substance being identified and measured in an analysis. For example, luminescent reactions can be used to detect and quantify proteases, lipases, phosphatases, peroxidases, glycosidases, and various metabolites such as ATP or NADH. Luminescent reactions can also be used to detect and quantify analytes through binding interactions, such as those mediated by antibodies and nucleotide probes. Typically, luminescent reactions can be used to detect less than $1\times10^{-16}$ moles of analyte in a sample, often less than $1\times10^{-19}$ moles. In luminescence, commonly detected analytes are the luciferases, especially firefly luciferase and *Renilla* luciferase. Most often these analytes are used to quantify phenomena associated with their creation through gene expression and protein synthesis. Other luminescent enzymes used as analytes include, but are not limited to, aequorin, *Vargula* luciferase, and other marine luciferases.

When using luminescence to measure an analyte, it is preferred that little or no light is produced by reactions that are not dependent on the presence of the analyte. This is the case with firefly luciferase. Under typical firefly luciferase assay conditions, luminescence cannot be detected when the firefly luciferase is not present. In contrast to assays employing firefly luciferase, light can generally be detected in *Renilla* luciferase assay systems when the *Renilla* luciferase is not present. Luminescence that is not dependent on the catalytic activity of a luminescent enzyme is termed autoluminescence. For example, autoluminescence can be caused by spontaneous oxidation of the luminogenic substrate coelenterazine.

Luminescence that is not dependent on the on the presence of an analyte (e.g. autoluminescence) can limit the usefulness of an analytical assay by reducing the ability to accurately measure the quantity of light resulting from the activity of the analyte. In particular, the sensitivity of luminescent assays containing coelenterazine or its structural analogs is reduced due to autoluminescence. Additionally, the addition of various components to the assay system, such as lipids (especially above the critical micelle concentration or CMC), hydrophobic proteins (especially those with a defined three-dimensional structure), and cells or other biological materials containing hydrophobic microenvironments, can greatly increase autoluminescence.

Assay sensitivity may also be reduced by luminescence from an unrelated luminogenic molecule. The unrelated luminogenic molecule may be present due to contamination of the analytical assay, or due to a separate analytical luminescence assay performed in the same reaction mixture. In either case, the sensitivity of an analytical luminescence assay could be improved by reducing the luminescence that is not dependent on the presence of the analyte.

SUMMARY OF THE INVENTION

Applicants have discovered that the sensitivity of luminescence assays can be improved by carrying out the assay in the presence of one or more organic compounds that reduce analyte-independent luminescence. In particular, Applicant has unexpectedly discovered that the analyte-independent luminescence can be reduced without similarly reducing analyte-dependent luminescence. Preferably, the analyte-dependent luminescence is reduced by a lower fold than the analyte-independent luminescence, or the analyte dependent luminescence remains about the same or increases. Accordingly, the invention provides a method for increasing the sensitivity of a luminescent assay comprising carrying out the assay in the presence of an organic compound that reduces luminescence that is not dependent on the presence of an analyte by a factor of at least about 10 fold, and that reduces luminescence that is dependent on the presence of an analyte by less than about 7 fold.

The invention also provides a method for increasing the sensitivity of a luminescent assay comprising carrying out the assay in the presence of an organic compound that reduces luminescence generated by luminogenic molecules not bound to an enzyme by at least about 10 fold, and that reduces the luminescence generated by luminogenic molecules bound to an enzyme by less than about 7 fold.

The invention also provides a method for increasing the sensitivity of a luminescent assay comprising carrying out the assay in the presence of an organic compound that reduces autoluminescence by at least about 10 fold, and that reduces luminescence that is dependent on the presence of an analyte by less than about 7 fold.

The invention also provides a method for increasing the sensitivity of a luminescent assay comprising carrying out the assay in the presence of an organic compound that comprises a selenium atom.

The invention also provides a method for increasing the sensitivity of a luminescent assay comprising carrying out the assay in the presence of an organic compound that comprises a carbon-selenium bond.

The invention also provides a method for increasing the sensitivity of a luminescent assay comprising carrying out the assay in the presence of an organic compound that comprises a carbon selenium double bond (C=Se).

The invention also provides a method for increasing the sensitivity of a luminescent assay comprising carrying out the assay in the presence of an organic compound that comprises a carbon-selenium single bond (C—Se)

The invention also provides a method for increasing the sensitivity of a luminescent assay comprising carrying out the assay in the presence of an organic compound that comprises a carbon-sulfur double bond (C=S).

The invention also provides a method for increasing the sensitivity of a luminescent assay comprising carrying out the assay in the presence of an organic compound that comprises a carbon atom bound to both a selenium atom and a nitrogen atom.

The invention also provides a method for increasing the sensitivity of a luminescent assay comprising carrying out the assay in the presence of an organic compound that comprises a carbon atom bound to both a sulfur atom and a nitrogen atom.

The invention also provides a method for increasing the sensitivity of a luminescent assay comprising carrying out the assay in the presence of an organic compound that comprises a sulfur atom bound to two carbon atoms, wherein the analyte-independent luminescence is reduced by at least about 10 fold. Preferably, the analyte-dependent luminescence is reduced by less than 7 fold.

The invention also provides an assay kit comprising packaging material containing 1) a luminogenic substrate of a luminescent enzyme, or a luminogenic enzyme; and 2) an organic compound for increasing the sensitivity of a luminescent assay. Preferably, the organic molecule is capable of 1) reducing the luminescence that is not dependent on the presence of an analyte by a factor of at least about 10 fold, and reducing the luminescence that is dependent on the presence of an analyte by less than about 7 fold; 2) reducing the luminescence generated by luminogenic molecules not bound to an enzyme by at least about 10 fold, and reducing the luminescence generated by luminogenic molecules bound to an enzyme by less than 7 fold; or 3) reducing autoluminescence by at least about 10 fold, and reducing luminescence that is dependent on the presence of an analyte by less than about 7 fold.

The invention also provides novel compounds disclosed herein that are useful to increase the sensitivity of a luminescent assay.

DETAILED DESCRIPTION

Figure 1:
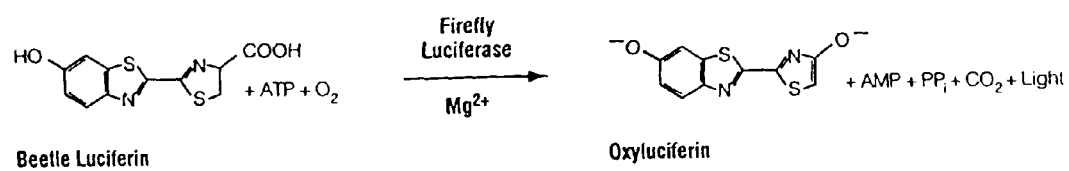
FIG. 1 illustrates chemiluminescent reaction catalyzed by firefly luciferase.
Figure 2:
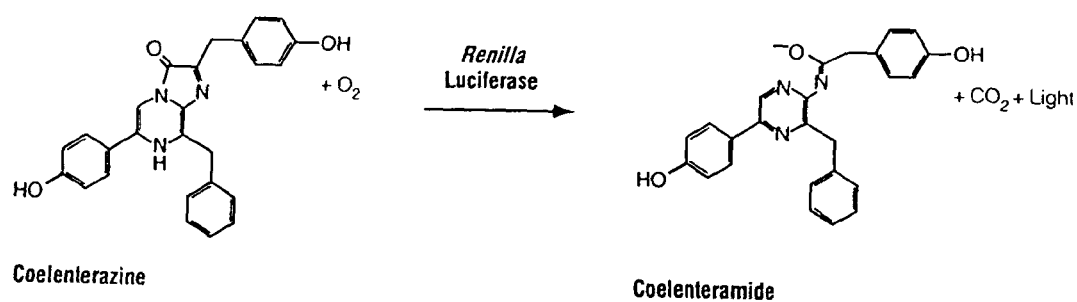
FIG. 2 illustrates chemiluminescent reaction catalyzed by Renilla luciferase.
Figure 3:
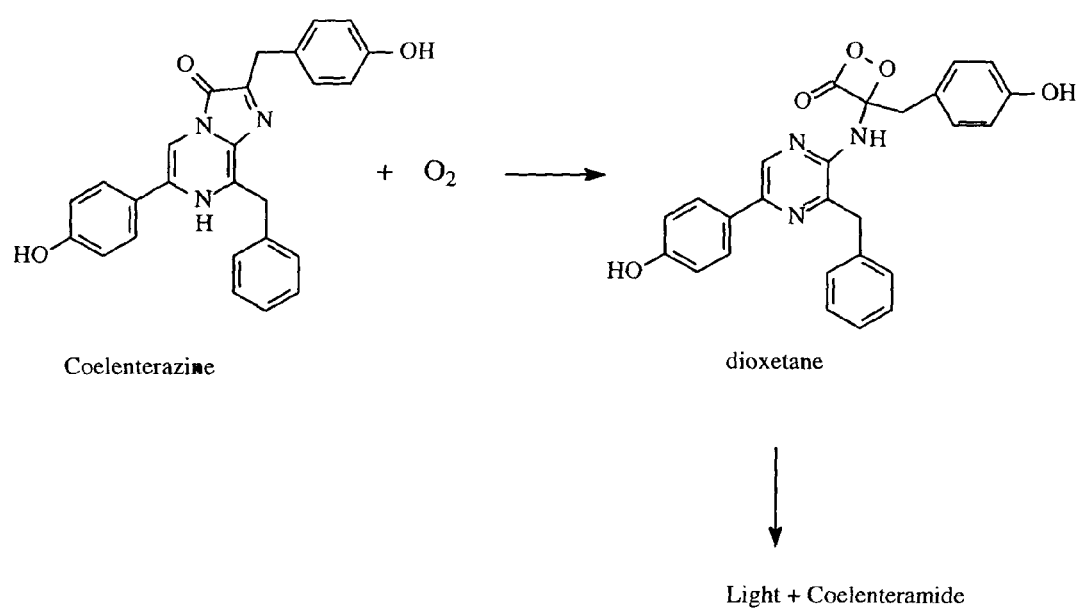
FIG. 3 illustrates a dioxetane intermediate in the colenterazine autoluminescence pathway.

Before the present invention is disclosed and described in detail, it is to be understood that this invention is not limited to specific assay formats, materials or reagents, as such may vary. It is also to be understood that the terminology used herein is for the purpose of describing particular embodiments only and is not intended to be limiting.

As used in the specification and the appended claims, the singular forms "a", "an" and "the" include plural referents unless the context clearly dictates otherwise. In this specification and in the claims that follow, reference will be made to a number of terms that shall be defined to have the following meanings, unless otherwise described:

The term "halo" as used herein denotes fluoro, chloro, bromo, or iodo.

The terms "Alkyl", "alkoxy", "alkenyl", "alkynyl", etc. as used herein denote both branched and unbranched groups; but reference to an individual radical such as "propyl" embraces only the straight, unbranched chain radical, a branched chain isomer such as "isopropyl" being specifically referred to.

The term "Aryl", as used herein, denotes a monocyclic or polycyclic hydrocarbon radical comprising 6 to 30 atoms wherein at least one ring is aromatic. Preferably, aryl denotes a phenyl radical or an ortho-fused bicyclic carbocyclic radical having about nine to ten ring atoms in which at least one ring is aromatic. "Heteroaryl" encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$–$C_4$) alkyl, phenyl or benzyl, as well as a radical of a polycyclic ring comprising 8 to 30 atoms derived therefrom. Preferably, heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$–$C_4$) alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "analyte", as used herein is a substance to be detected in a test sample. In luminescence assays, commonly detected analytes include the luciferases, especially firefly luciferase and Renilla luciferase. Other luminescent enzymes used as analytes include, but are not limited to, aequorin, Vargula luciferase, and other marine luciferases. Additionally, luminescent reactions can be used to detect and quantify analytes such as proteases, lipases, phosphatases, peroxidases, glycosidases, and various metabolites such as ATP or NADH. Luminescent reactions can also be used to detect and quantify analytes through binding interactions, such as those mediated by antibodies and nucleotide probes. In certain cases, analyte-dependent luminescence can be coupled to the activity of a luminescent enzyme. For example, alkaline phosphatase (AP) could be detected by using a phospho derivative of luciferin. By this strategy, luciferin is generated by the action of AP, which then yields light by reaction with luciferase. The instant invention would allow the AP assay to be run after a separate horseradish peroxidase/luminol reaction. With respect to the analyte AP, a compound as described herein, could be added to reduce the analyte-independent luminescence caused by horseradish peroxidase.

The term "autoluminesence" as used herein, refers to the release of light from a luminogenic molecule that does not result from enzymatic action on the luminogenic molecule.

The term "increase the sensitivity of a luminescent assay" as used herein means increasing the precision of the assay or improving the ability to measure the presence of a small amount of an analyte with the assay. For example, the sensitivity of a luminescent assay can be increased by reducing analyte-independent luminescence. Preferably, analyte-independent luminescence is reduced, and a minimal reduction, no reduction, or an increase in analyte-dependent luminescence results. Additionally, analyte-independent luminesence is preferably reduced by a greater fold than analyte-dependent luminescence.

The term "luminescent," as used herein, includes bio-luminescence (i.e light produced by a living organism), chemi-luminescence (light produced when a chemical reaction proceeds), and electrochemical-luminescence. When the enzyme involved has evolved in an organism by natural selection for the purpose of generating light, or the enzyme involved is a mutated derivative of such an enzyme, the luminescent reactions are also called "bioluminescent reactions" and the enzyme involved is also called a "bioluminescent enzyme." Examples are firefly luciferase, *Renilla* luciferase, *Cypridina* luciferase, Aequorin photoprotein, Obelin photoprotein, and the like.

The term "luminescent assay" or "luminescence assay" includes any assay that generates light based on the presence of an analyte. Such assays include assays that employ one or more luciferase enzymes (e.g. firefly luciferase, *Renilla* luciferase, *Cypridina* luciferase, and the like).

The term "luminogenic enzyme," as used herein includes enzymes that catalyze a reaction that produces light, or that lead to the production of light. For example, the term includes firefly luciferase, *Renilla* luciferase, *Cypridina* luciferase, Aequorin photoprotein, Obelin photoprotein, and the like.

The term "luminogenic molecule" as used herein refers to a molecule capable of creating light via a chemical reaction (e.g. luciferin, coelenterazine, or a functional analog thereof). Generally, a luminogenic molecule is either a high energy molecular species (e.g. a stabilized dioxetane), or it is transformed into a high energy molecular species by a chemical reaction. The chemical reaction is usually oxidation by oxygen, superoxide, or peroxide. In each case, the energy within the luminogenic molecule is released by the chemical reaction. Although at least some of this energy is released as photons of light, the energy can also be released in other forms, such as heat. The luminogenic molecules that do not yield light disperse their energy through alternative modes, often termed "dark pathways".

The term "luminogenic molecule not bound to an enzyme" as used herein, includes a luminogenic molecule that is not bound to an enzyme (e.g. firefly luciferase, *Renilla* luciferase, *Cypridina* luciferase, and the like) that catalyzes a reaction that produces light.

The term "luminogenic molecules bound to an enzyme" as used herein includes a luminogenic molecule that is bound to an enzyme that catalyzes a reaction that produces light.

The term "luminescence that is dependent on the presence of an analyte," or "analyte-dependent luminescence" as used herein, includes luminescence that results from a chemical reaction that involves an analyte, as well as luminescence that correlates with the presence of an analyte either directly or indirectly.

The term "luminescence that is not dependent on the presence of an analyte," or "analyte-independent luminescence" as used herein, includes luminescence resulting from autoluminescence of a luminogenic substrate as well as luminescence resulting from an unrelated luminogenic molecule present in an assay mixture.

The term "quench" as used herein means to reduce the yield of photons from a luminescent reaction. The term includes preventing an analyte from being detected or being detectable, and may occur either directly or indirectly. Agents that can be used to quench a reaction are known as "quenching agents."

Applicant has discovered that it is possible to increase the sensitivity of a luminescent assay by carrying out the assay in the presence of an organic compound that reduces analyte-independent luminescence. This finding is unexpected. Using procedures similar to those described herein, one skilled in the art can identify compounds that are suitable for increasing the sensitivity of a luminescent assay. The structure of the compound is not critical provided the compound is capable of increasing the sensitivity of a luminescent assay.

In particular, applicant has discovered that compounds that comprise a sulfur atom or a selenium atom are particularly useful for increasing the sensitivity of a luminescent assay. The remaining chemical structure of the compound that comprises a selenium atom or a sulfur atom is not critical, provided the structure does not interfere with the function of the compound. Preferred compounds have low toxicity at concentrations used in the invention, and can be stored, transported, and disposed of inexpensively.

Suitable compounds include organic compounds (i.e. compounds that comprise one or more carbon atoms). Suitable organic compounds can comprise a carbon-sulfur bond or a carbon-selenium bond, for example suitable organic compounds can comprise a carbon-sulfur double bond (C=S), a carbon selenium double bond (C=Se), a carbon-sulfur single bond (C—S), or carbon-selenium single bond (C—Se). Suitable organic compounds can also comprise a carbon bound mercapto group (C—SH) or a sulfur atom bound to two catbon atoms (C—S—C). Preferred compounds are lipophyllic in nature.

Suitable compounds that comprise a carbon sulfur double bond or a carbon selenium double bond include for example compounds of formula (I):

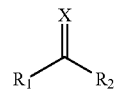

wherein X is S or Se; $R_1$ and $R_2$ are each independently hydrogen, $(C_1-C_{20})$alkyl, $(C_3-C_8)$cycloalkyl, $(C_1-C_{20})$alkoxy, $(C_2-C_{20})$alkenyl, $(C_2-C_{20})$alkynyl, aryl, heteroaryl, or $NR_aR_b$; or $R_1$ and $R_2$ together with the carbon to which they are attached form a 5, 6, 7, or 8 membered saturated or unsaturated ring comprising carbon and optionally comprising 1, 2, or 3 heteroatoms selected from oxy (—O—), thio (—S—), or nitrogen (—$NR_c$)—, wherein said ring is optionally substituted with 1, 2, or 3 halo, hydroxy, oxo, thioxo, carboxy, $(C_1-C_{20})$alkyl, $(C_3-C_8)$cycloalkyl, $(C_1-C_{20})$alkoxy, $(C_1-C_{20})$alkanoyl, $(C_1-C_{20})$alkoxycarbonyl, ($C_2$–$C_{20}$)alkenyl, ($C_2$–$C_{20}$)alkynyl, aryl, or heteroaryl; and $R_a$, $R_b$ and $R_c$ are each independently hydrogen, ($C_1$–$C_{20}$)alkyl, ($C_3$–$C_8$)cycloalkyl, ($C_2$–$C_{20}$)alkenyl, ($C_1$–$C_{20}$)alkanoyl, ($C_1$–$C_{20}$)alkoxycarbonyl, ($C_2$–$C_{20}$)alkynyl, aryl, heteroaryl; wherein any ($C_1$–$C_{20}$)alkyl, ($C_3$–$C_8$)cycloalkyl, ($C_1$–$C_{20}$)alkoxy, ($C_2$–$C_{20}$)alkenyl ($C_1$–$C_{20}$)alkanoyl, ($C_1$–$C_{20}$)alkoxycarbonyl, or ($C_2$–$C_{20}$)alkynyl of $R_1$, $R_2$, $R_a$, $R_b$, and $R_c$ is optionally substituted with one or more (e.g 1, 2, 3, or 4) halo, hydroxy, mercapto, oxo, thioxo, carboxy, ($C_1$–$C_{20}$)alkanoyl, ($C_1$–$C_{20}$)alkoxycarbonyl, aryl, or heteroaryl; and wherein any aryl or heteroaryl is optionally substituted with one or more (1, 2, 3, or 4) halo, hydroxy, mercapto, carboxy, cyano, nitro, trifluoromethyl, trifluoromethoxy, ($C_1$–$C_{20}$)alkanoyl, ($C_1$–$C_{20}$)alkanoyloxy, sulfo or ($C_1$–$C_{20}$)alkoxycarbonyl; or a salt thereof.

Suitable compounds that comprise a mercapto group include for example compounds of the formula $R_3SH$ wherein: $R_3$ is ($C_1$–$C_{20}$)alkyl, ($C_3$–$C_8$)cycloalkyl, ($C_2$–$C_{20}$)alkenyl, ($C_2$–$C_{20}$)alkynyl, aryl, or heteroaryl; wherein any ($C_1$–$C_{20}$)alkyl, ($C_3$–$C_8$)cycloalkyl, ($C_2$–$C_{20}$)alkenyl, or ($C_2$–$C_{20}$)alkynyl of $R_3$ is optionally substituted with one or more (e.g 1, 2, 3, or 4) halo, hydroxy, mercapto oxo, thioxo, carboxy, ($C_1$–$C_{20}$)alkanoyl, ($C_1$–$C_{20}$)alkoxycarbonyl, aryl, heteroaryl, or $NR_dR_e$; wherein $R_d$ and $R_e$ are each independently hydrogen, ($C_1$–$C_{20}$)alkyl, ($C_3$–$C_8$)cycloalkyl, ($C_2$–$C_{20}$)alkenyl, ($C_2$–$C_{20}$)alkynyl, ($C_1$–$C_{20}$)alkanoyl, ($C_1$–$C_{20}$)alkoxycarbonyl aryl, or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy, ($C_1$–$C_{20}$)alkanoyl, ($C_1$–$C_{20}$)alkanoyloxy, sulfo or ($C_1$–$C_{20}$)alkoxycarbonyl; or a salt thereof.

Other suitable compounds include for example compounds of the formula $R_4NCS$ wherein: $R_4$ is ($C_1$–$C_{20}$)alkyl, ($C_3$–$C_8$)cycloalkyl, ($C_2$–$C_{20}$)alkenyl, ($C_2$–$C_{20}$)alkynyl, aryl, or heteroaryl; wherein any ($C_1$–$C_{20}$)alkyl, ($C_3$–$C_8$)cycloalkyl, ($C_2$–$C_{20}$)alkenyl, or ($C_2$–$C_{20}$)alkynyl of $R_3$ is optionally substituted with one or more (e.g 1, 2, 3, or 4) halo, hydroxy, mercapto oxo, thioxo, carboxy, ($C_1$–$C_{20}$)alkanoyl, ($C_1$–$C_{20}$)alkoxycarbonyl, aryl, heteroaryl, or $NR_fR_g$; wherein $R_f$ and $R_g$ are each independently hydrogen, ($C_1$–$C_{20}$)alkyl, ($C_3$–$C_8$)cycloalkyl, ($C_2$–$C_{20}$)alkenyl, ($C_2$–$C_{20}$)alkynyl, ($C_1$–$C_{20}$)alkanoyl, ($C_1$–$C_{20}$)alkoxycarbonyl aryl, or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy, ($C_1$–$C_{20}$)alkanoyl, ($C_1$–$C_{20}$)alkanoyloxy, sulfo or ($C_1$–$C_{20}$)alkoxycarbonyl; or a salt thereof.

Other suitable compounds that comprise a carbon-selenium single bond or a carbon sulfur single bond include compounds of formula $R_5$—X—$R_6$ wherein:

X is —S— or —Se—;

$R_5$ is ($C_1$–$C_{20}$)alkyl, ($C_3$–$C_8$)cycloalkyl, ($C_2$–$C_{20}$)alkenyl, ($C_2$–$C_{20}$)alkynyl, aryl, or heteroaryl; and $R_6$ is hydrogen, ($C_1$–$C_{20}$)alkyl, ($C_3$–$C_8$)cycloalkyl, ($C_2$–$C_{20}$)alkenyl, ($C_2$–$C_{20}$)alkynyl, aryl, or heteroaryl;

or $R_5$ and $R_6$ together with X form a heteroaryl;

wherein any ($C_1$–$C_{20}$)alkyl, ($C_3$–$C_8$)cycloalkyl, ($C_2$–$C_{20}$)alkenyl, or ($C_2$–$C_{20}$)alkynyl of $R_5$ or $R_6$ is optionally substituted with one or more (e.g 1, 2, 3, or 4) halo, hydroxy, mercapto oxo, thioxo, carboxy, ($C_1$–$C_{20}$)alkanoyl, ($C_1$–$C_{20}$)alkoxycarbonyl, aryl, heteroaryl, or $NR_kR_m$;

wherein $R_k$ and $R_m$ are each independently hydrogen, ($C_1$–$C_{20}$)alkyl, ($C_3$–$C_8$)cycloalkyl, ($C_2$–$C_{20}$)alkenyl, ($C_2$–$C_{20}$)alkynyl, ($C_1$–$C_{20}$)alkanoyl, ($C_1$–$C_{20}$)alkoxycarbonyl aryl, or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy, ($C_1$–$C_{20}$)alkanoyl, ($C_1$–$C_{20}$)alkanoyloxy, sulfo or ($C_1$–$C_{20}$)alkoxycarbonyl; or a salt thereof.

Specific and preferred values listed below for radicals, substituents, and ranges, are for illustration only; they do not exclude other defined values or other values within defined ranges for the radicals and substituents Specifically, ($C_1$–$C_{20}$)alkyl can be methyl, ethyl, propyl, isopropyl, butyl, iso-butyl, sec-butyl, pentyl, 3-pentyl, or hexyl; ($C_3$–$C_8$)cycloalkyl can be cyclopropyl, cyclobutyl, cyclopentyl, or cyclohexyl; ($C_1$–$C_{20}$)alkoxy can be methoxy, ethoxy, propoxy, isopropoxy, butoxy, iso-butoxy, sec-butoxy, pentoxy, 3-pentoxy, or hexyloxy; ($C_2$–$C_{20}$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$–$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$–$C_{20}$)alkanoyl can be acetyl, propanoyl or butanoyl; ($C_1$–$C_{20}$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_2$–$C_{20}$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specifically, $R_1$ and $R_2$ can each independently be hydrogen, ($C_1$–$C_{20}$)alkyl, ($C_3$–$C_8$)cycloalkyl, ($C_2$–$C_{20}$)alkenyl, ($C_2$–$C_{20}$)alkynyl, aryl, heteroaryl, or $NR_aR_b$; wherein $R_a$ and $R_b$ are each independently hydrogen, ($C_1$–$C_{20}$)alkyl, ($C_3$–$C_8$)cycloalkyl, ($C_2$–$C_{20}$)alkenyl, ($C_1$–$C_{20}$)alkanoyl, ($C_1$–$C_{20}$)alkoxycarbonyl, ($C_2$–$C_{20}$)alkynyl, aryl, or heteroaryl; wherein any ($C_1$–$C_{20}$)alkyl, ($C_3$–$C_8$)cycloalkyl, ($C_1$–$C_{20}$)alkoxy, ($C_2$–$C_{20}$)alkenyl ($C_1$–$C_{20}$)alkanoyl, ($C_1$–$C_{20}$)alkoxycarbonyl, or ($C_2$–$C_{20}$)alkynyl of $R_1$, $R_2$, $R_a$, and $R_b$ is optionally substituted with 1 or 2 halo, hydroxy, mercapto, oxo, thioxo, carboxy, ($C_1$–$C_{20}$)alkanoyl, ($C_1$–$C_{20}$)alkoxycarbonyl, aryl, or heteroaryl; and wherein any aryl or heteroaryl is optionally substituted with one or more halo, hydroxy, mercapto, carboxy, cyano, nitro, trifluoromethyl, trifluoromethoxy, ($C_1$–$C_{20}$)alkanoyl, ($C_1$–$C_{20}$)alkanoyloxy, sulfo or ($C_1$–$C_{20}$)alkoxycarbonyl.

Specifically, $R_1$ and $R_2$ can each independently be hydrogen, ($C_1$–$C_{20}$)alkyl, ($C_2$–$C_{10}$)alkenyl, ($C_2$–$C_{10}$)alkynyl, aryl, or $NR_aR_b$.

Specifically, $R_1$ and $R_2$ together with the carbon to which they are attached can form a 5 or 6 membered saturated or unsaturated ring comprising carbon and optionally comprising 1 or 2 heteroatoms selected from oxy (—O—), thio (—S—), or nitrogen (—$NR_c$)—, wherein said ring is optionally substituted with 1, 2, or 3 halo, hydroxy, oxo, thioxo, carboxy, ($C_1$–$C_{20}$)alkyl, ($C_3$–$C_8$)cycloalkyl, ($C_1$–$C_{20}$)alkoxy, ($C_1$–$C_{20}$)alkanoyl, ($C_1$–$C_{20}$)alkoxycarbonyl, ($C_2$–$C_{20}$)alkenyl, ($C_2$–$C_{20}$)alkynyl, aryl, or heteroaryl; wherein $R_c$ is hydrogen, ($C_1$–$C_{20}$)alkyl, ($C_3$–$C_{20}$)cycloalkyl, ($C_2$–$C_{20}$)alkenyl, ($C_1$–$C_{20}$)alkanoyl, ($C_1$–$C_{20}$)alkoxycarbonyl, ($C_2$–$C_{20}$)alkynyl, aryl, heteroaryl; wherein any ($C_1$–$C_{20}$)alkyl, ($C_3$–$C_{20}$)cycloalkyl, ($C_1$–$C_{20}$)alkoxy, ($C_2$–$C_{20}$)alkenyl ($C_1$–$C_{20}$)alkanoyl, ($C_1$–$C_{20}$)alkoxycarbonyl, or ($C_2$–$C_{20}$)alkynyl of $R_1$, $R_2$, and $R_c$ is optionally substituted with one or more halo, hydroxy, mercapto, oxo, thioxo, carboxy, $(C_1-C_{20})$alkanoyl, $(C_1-C_{20})$alkoxycarbonyl, aryl, or heteroaryl; and wherein any aryl or heteroaryl is optionally substituted with one or more halo, hydroxy, mercapto, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl.

Specifically, $R_1$ and $R_2$ can each independently be $NR_aR_b$; wherein $R_a$ and $R_b$ are each independently hydrogen, $(C_1-C_{20})$alkyl, $(C_3-C_8)$cycloalkyl, $(C_2-C_{20})$alkenyl, $(C_1-C_{20})$alkanoyl, $(C_1-C_{20})$alkoxycarbonyl, $(C_2-C_{20})$alkynyl, aryl, heteroaryl; wherein any $(C_1-C_{20})$alkyl, $(C_3-C_8)$cycloalkyl, $(C_2-C_{20})$alkenyl $(C_1-C_{20})$alkanoyl, $(C_1-C_{20})$alkoxycarbonyl, or $(C_2-C_{20})$alkynyl is optionally substituted with one or more halo, hydroxy, mercapto, oxo, thioxo, carboxy, aryl, or heteroaryl; and wherein any aryl or heteroaryl is optionally substituted with one or more halo, hydroxy, mercapto, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl.

Specifically, $R_1$ and $R_2$ can each independently be amino, $(C_1-C_{20})$alkyl, $(C_1-C_{20})$alkylamino, allylamino, 2-hydroxyethylamino, phenylamino, or 4-thiazoylamino.

Specifically, $R_1$ and $R_2$ can each independently be amino, methyl, allylamino, 2-hydroxyethylamino, phenylamino, or 4-thiazoylamino.

A specific value for $R_3$ is $(C_1-C_{20})$alkyl optionally substituted with one or more halo, mercapto oxo, thioxo, carboxy, $(C_1-C_{20})$alkanoyl, $(C_1-C_{20})$alkoxycarbonyl, aryl, heteroaryl, or $NR_dR_e$.

A specific value for $R_3$ is 2-aminoethyl, 2-amino-2-carboxyethyl, or 2-acylamino-2-carboxyethyl.

A specific value for $R_4$ is aryl, optionally substituted with one or more halo, mercapto, hydroxy, oxo, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl.

Specifically, $R_5$ is $(C_1-C_{10})$alkyl, $(C_3-C_6)$cycloalkyl, $(C_2-C_{10})$alkenyl, $(C_2-C_{10})$alkynyl, aryl, or heteroaryl; and $R_6$ is hydrogen, $(C_1-C_{10})$alkyl, $(C_3-C_6)$cycloalkyl, $(C_2-C_{10})$alkenyl, $(C_2-C_{10})$alkynyl, aryl, or heteroaryl.

Specifically, $R_5$ and $R_6$ together with X form a heteroaryl.

Preferred organic compounds exclude polypeptides and proteins comprising one or more mercapto (C—SH) groups.

Preferred organic compounds exclude compounds that comprise one or more mercapto (C—SH) groups.

Figure 4:
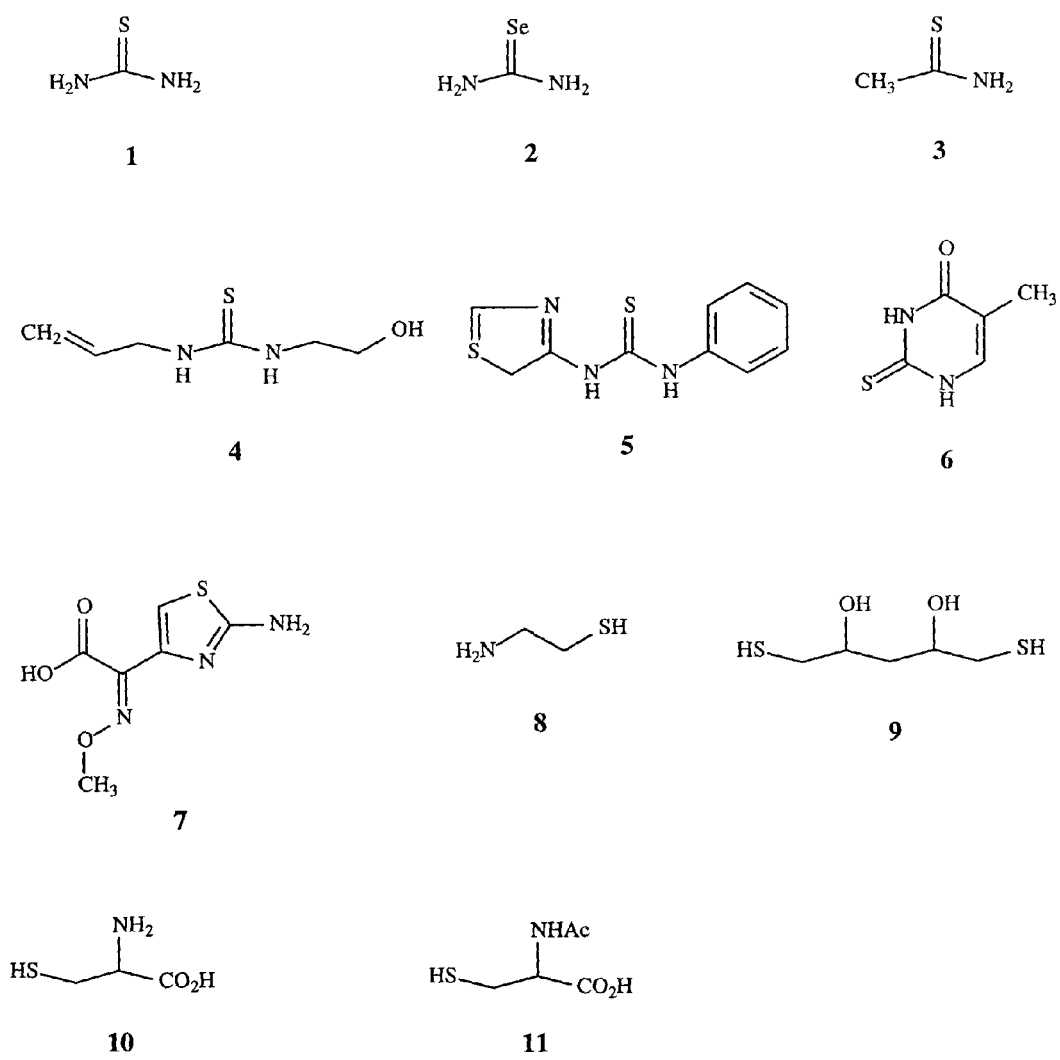
FIG. 4 shows representative compounds (1–11) that reduce auto luminescence.

A preferred organic compound is a compound of formula 1–11 as shown in FIG. 4. A more preferred compound is thiourea.

The compounds described hereinabove are available from commercial sources or can be prepared from commercially available starting materials using procedures that are known in the field of synthetic chemistry. For example, see Jerry March, Advanced Organic Chemistry, 4th ed. Wiley-Interscience, John Wiley and Sons, New York, 1992.

In cases where compounds are sufficiently basic or acidic to form stable salts, use of the compounds as salts in the methods of the invention may be appropriate. Examples of suitable salts include organic acid addition salts, for example, tosylate, methanesulfonate, acetate, citrate, malonate, tartarate, succinate, benzoate, ascorbate, α-ketoglutarate, and α-glycerophosphate salts. Suitable inorganic salts may also be formed, including hydrochloride, sulfate, nitrate, bicarbonate, and carbonate salts.

Salts can be obtained using standard procedures well known in the art, for example by reacting a sufficiently basic compound with a suitable acid. Alkali metal (for example, sodium, potassium or lithium) or alkaline earth metal (for example calcium) salts can also be used.

When used in accord with the methods of the invention, the compounds described herein can be present in a luminescence reaction at any concentration that increases the sensitivity of the assay. The optimum concentration of a given compound will depend on the luminescent reagent(s) employed, and on the specific conditions under which a given assay is carried out. However, suitable concentrations can be determined using standard techniques that are available in the art.

Specifically, the compound that can increase the sensitivity of the assay can be present in a luminescence reaction at a concentration of at least about 0.1 μM, or at a concentration of at least about 0.1 mM. More specifically, the compound can be present in the luminescence reaction at a concentration in the range from about 0.1 μM to about 500 mM (inclusive), or in the range from about 1 μM to about 250 mM (inclusive). Preferably, the compound is present at a concentration in the range from about 10 μM to about 100 mM (inclusive).

Specifically, the assay can be performed in the presence of whole cells.

Specifically, the assay can be carried out in a solvent comprising at least about 10% water. More specifically, the invention can be carried out in a solvent comprising at least about 25% water, or at least about 40% water.

Preferably, in the practice of the methods of the invention, the analyte-independent luminescence is reduced by at least about 10 fold, or more preferably by at least about 20 fold, at least about 50 fold, or at least about 100 fold in the present of a compound, while the analyte-dependent luminescence is reduced by less than about 7 fold, about 5 fold, about 3 fold, or about 2 fold. For example, a relative light unit value of 5 produced in the presence of the compound while a relative light unit value of 100 produced in the absence of the compound reflects a decrease in luminescence in the presence of the compound by 20 fold.

Preferably in the practice of the methods of the invention, the luminescence generated by luminogenic molecules not bound to an enzyme is reduced by at least about 10 fold, or more preferably by at least about 20 fold, at least about 50 fold, or at least about 100 fold, while the luminescence generated by luminogenic molecules bound to an enzyme is reduced by less than about 7 fold, about 5 fold, about 3 fold, or about 2 fold. The luminescence generated by luminonogenic molecules bound to an enzyme is preferably reduced by a lower fold than the fold decrease in luminescence generated by luminogenic molecules not bound to an enzyme.

Preferably in the practice of the methods of the invention, autoluminescence is reduced by at least about 10 fold, or more preferably by at least about 20 fold, at least about 50 fold, or at least about 100 fold, while luminescence that is dependent on the presence of an analyte is reduced by less than about 7 fold, about 5 fold, about 3 fold, or about 2 fold. The luminescence that is dependent on the presence of an analyte is preferably reduced by a lower fold than the fold decrease in autoluminescence.

Preferably in the practice of the methods of the invention, when an assay is carried out in the presence of a compound that comprises a sulfur atom or a selenium atom, analyte-independent luminescence is reduced by at least about 10 fold, or more preferably by at least about 20 fold, at least about 50 fold, or at least about 100 fold.

Preferably in the practice of the methods of the invention, when an assay is carried out in the presence of a compound that comprises a sulfur atom or a selenium atom, analyte-dependent luminescence is reduced by less than about 7 fold, about 5 fold, about 3 fold, or about 2 fold.

For kits of the invention the enzyme substrate, enzyme, and the compound can each be contained in a separate container, or they can be contained in a single container. The kit can optionally comprise a buffer solution suitable for use in a luminescent assay, and the enzyme substrate or enzyme, and the buffer solution can optionally be contained in a single container. Additionally, the compound and the buffer solution can optionally be contained in a single container. The kits can also optionally comprise a second substrate (e.g. a substrate for firefly luciferase or *Renilla* luciferase), or a quenching agent for a luminescent enzyme reaction. The kits can also optionally comprise ATP, or can optionally comprise both a luminogenic substrate of a luminescent enzyme, and a luminogenic enzyme.

The ability of a compound to increase the sensitivity of a luminescent assay can be determined using assays that are well known to the art, or using the assays described in the Examples herein below.

Compounds identified herein have been shown to be useful for increasing the sensitivity of luminescent assays. The compounds are particularly useful for reducing luminescence that results from the decomposition of intermediate dioxetane rings. Thus, in addition to being useful for increasing the sensitivity of luminescent assays (e.g. bioluminescent, chemiluminescent, or electroluminescent assays), the compounds are also useful for reducing luminescence in other systems that involve intermediate dioxetane rings and the like.

The invention will now be illustrated by the following non-limiting Examples. Compounds 1–11 (FIG. 4) are readily available from commercial sources.

EXAMPLE 1

Improved Assay Sensitivity

Experiments to assess the ability of representative organic compounds ("compounds") to increase luminescence assay sensitivity were performed under the conditions described below in Format A and Format B. Improved luminescence assay sensitivity is demonstrated by the ability of the compounds to decrease the analyte-independent luminescence resulting from the oxidation of coelenterazine, while causing lesser or minimal reduction to the analyte-dependent luminescence, i.e. coelenterazine in the presence of *Renilla* luciferase. It is demonstrated herein that the compound causes a lower-fold decrease in luminescence when the analyte of interest is present than the fold decrease in luminescence when the analyte of interest is absent. The enzymatic luminescence measurement may have an autoluminescence component.

In fact, for the majority of experiments described herein, an increase in the enzymatic luminescence measurement was observed when the compound being tested was present. Because autoluminescence is typically very low, in order to observe a more pronounced effect of the compounds on autoluminescence, autoluminescence was enhanced by adding a detergent, increasing the pH, adding hydrogen peroxide, adding DMSO, adding BSA, or adding sodium hydrosulfite.

Format A Assays were performed in the presence of Steady Glo® reagent (SG) and Stop & Glo® reagent (S+G), (Promega Corporation, Madison Wis.). A total reaction volume of 150 µl consisted of:

50 µl F-12 (Ham) media+1 mg/ml gelatin (with or without enzyme[1])

50 µl S+G (containing substrate[2])

50 µl SG

[1] *Renilla* luciferase enzyme was added to F-12 cell culture media containing 1% gelatin, to a concentration of approximately 2.5ng/50 µl media. Reactions in the absence of *Renilla* luciferase reveal the effect of the compound on autoluminescence while reactions in the presence of enzyme reveal the effect of the compound on *Renilla* luciferase-catalyzed luminescence.

[2] The S+G reagent was prepared as per manufacturer's instructions, with the exception that for these experiments a S+G solvent three times more concentrated than normal was used to resuspend the S+G substrate. Under these conditions, a higher concentration of coelenterazine in the S+G was needed for substrate to reach saturation conditions.

The compound to be tested was re-suspended in either SG or S+G reagent to a final concentration of SG or S+G of (1×). The compound was added so the final concentration in the 150 µl total volume would be that listed in Table 1 and the reagent was diluted to the a final of 50 µl with water. For controls, the SG or S+G reagent was brought up to 50 µl with water or with the solvent used to dissolve the compound of interest. For example, if a compound needed to be dissolved in DMSO (dimethyl sulphoxide), an equal volume of DMSO was added to the control reaction. Unless otherwise indicated, the compounds were first dissolved in water. The same result can be obtained by adding the compound to be tested directly to the media portion of the reaction instead of to the SG or S+G.

For each concentration of a particular compound, a mixture containing all of the components in sufficient amounts for four reactions (i.e. 200 µl media, 200 µl SG, 200 µl S+G) was assembled. From this mixture, 150 µl was dispensed into triplicate wells on a 96-well plate. Alternatively, reactions were sometimes assembled in each well of the plate by adding each of the 50 µl portions and mixing. The plate was incubated at 22° C. and after 5 minutes the luminescence was measured using a Dynex plate luminometer (1 second measurement per well).

Format B Experiments were performed in a reaction volume of 150 µl Matthew's Buffer (referred to herein as MB) as either a standard MB composition or a modified MB composition as described below. As with Format A, reactions with and without *Renilla* luciferase were carried out to observe the effect of the organic compounds on assay sensitivity. In order to be able to add the reaction components such as enzyme, substrate, detergent, and compound to be tested; the reaction was assembled in 3 portions as follows:

| | |
|---|---|
| 50 µl MB | (with or without enzyme[3]) |
| 50 µl MB with Coelenterazine | (with or without detergent[4]) |
| 50 µl MB | (with or without compound[5]) |

[3] Enzyme was added to 1X MB to a concentration of approximately 2.5 ng/50 µl buffer
[4] Detergents are known to increase the level of autoluminescence. For completeness, the effect of the compounds on autoluminescence and on enzymatic luminescence was evaluated in the presence and absence of detergent.
[5] 2X MB was used to make 1X MB with the compound to be tested at various concentrations and water. For controls, 1X MB was made with only water or with water and the addition of the solvent used to solubilize the compound to be tested. For example, if the compound to be tested was dissolved in DMSO, an equal amount of only DMSO was added to the control MB sample.

1× Matthew's buffer standard composition consists of:
  100 mM potassium phosphate
  500 mM sodium chloride
  1 mM ethylenediaminetetraacetic acid (EDTA)
  0.1 mg/ml bovine serum albumin (BSA)
  pH 7.4

The BSA functions as an enzyme stabilizer and, in the standard MB composition, enhances coelenterazine autoluminescence but not to the extent of the autoluminescence generated when detergent is present. In order to observe the autoluminescence enhanced only by the detergent, for the majority of the experiments, BSA was replaced with porcine gelatin as the enzyme stabilizer at a final concentration of 0.15 mg/ml or 0.45 mg/ml. Taking all the variants into account the format can be sub-divided in 4 different versions:

| | |
|---|---|
| B1 | BSA/Detergent |
| B2 | BSA/No Detergent |
| B3 | Gelatin/Detergent |
| B4 | Gelatin/No Detergent |

Reactions were carried out in triplicate by adding each of the 50 μl portions to microtiter plate wells and mixing. The resulting relative light units generated per well was measured immediately using a Dynex MLX Microtiter plate luminometer or a Wallac 1450 MicroBeta Trilux plate luminometer (1 second/well) or alternatively, the plate was incubated at 22° C. and read after 5 minutes in the same fashion.

Results in Table 1 herein below are shown as:

a) fold-decrease in non-enzymatic autoluminescence measurement in the presence of the compound when compared to the absence of the compound and, b) effect of the compound on enzymatic luminescence measurement in the presence of the compound when compared to control samples lacking only the compound.

For example, a result of "decreased 7.4 fold" indicates that the luminescence measurement in the presence of the compound was 7.4 times less than the luminescence measurement in the absence of the compound. In all cases, the fold decrease in luminescence not associated with the presence of *Renilla* luciferase (autoluminescence) was greater than the fold decrease in luminescence associated with the presence of *Renilla* luciferase. Thus, the compounds reduce the luminescence not associated with enzymatic activity of the analyte to a greater degree than the luminescence associated with the enzymatic activity of the analyte.

TABLE 1

See FIG. 4 for compound identity.
Format overview:
A Media:Steady Glo:Stop & Glo
B1 Matthew's Buffer with BSA and detergent
B2 Matthew's Buffer with BSA without detergent
B3 Matthew's Buffer with gelatin and detergent
B4 Matthew's Buffer with gelatin without detergent

| Compound | mM compound (in final soln) | Format | Fold decrease autoluminescence | Effect on luminescence |
|---|---|---|---|---|
| 1 | 33 | A | 15 | No effect |
| 1 | 316 | B2 | 2 | Increased 1.2 fold |
| 1 | 10 | B4 | 2 | Increased 2.1 fold |
| 1 | 100 | B3 | 290 | No effect |
| 1 | 100 | B4 | 8.5 | Increased 1.4 fold |
| 1 | 50 | B3 + 17% DMSO | 500 | Increased 5 fold |
| 1 | 50 | B4 + 17% DMSO | 15 | Increased 7 fold |
| 1 | 3 | B3 + 10 mM sodium hydrosulfate | 21.8 | Decreased 7.4 fold |
| 1 | 3 | B4 + 10 mM sodium hydrosulfate | 2.6 | No effect |
| 1 | 3 | B3 | 120 | No effect |

TABLE 1-continued

See FIG. 4 for compound identity.
Format overview:
A Media:Steady Glo:Stop & Glo
B1 Matthew's Buffer with BSA and detergent
B2 Matthew's Buffer with BSA without detergent
B3 Matthew's Buffer with gelatin and detergent
B4 Matthew's Buffer with gelatin without detergent

| Compound | mM compound (in final soln) | Format | Fold decrease autoluminescence | Effect on luminescence |
|---|---|---|---|---|
| 1 | 3 | B3 with Tween-20 | 100 | No effect |
| 1 | 3 | B3 with Zwittergent | 6 | Increased 1.6 fold |
| 4 | 10 | A | 3 | No effect |
| 4 | 30 | B3 | 500 | Decreased 4.6 fold |
| 4 | 30 | B4 | 3.9 | Increased 1.2 fold |
| 5 | 10 | A | 115 | Decreased 10 fold |
| 6 | 32 | A + 17% DMSO | 65 | Decreased 1.5 fold |
| 6 | 32 | B3 + 33% DMSO | 660 | Increased 1.6 fold |
| 6 | 32 | B4 + 33% DMSO | 120 | Increased 4.7 fold |
| 2 | 10 | A | 100 | No effect |
| 2 | 10 | B3 | 70 | No effect |
| 3 | 33 | A | 100 | Increased 1.2 fold |
| 3 | 33 | B3 | 545 | Increased 1.2 fold |
| 3 | 33 | B4 | 3.4 | Increased 2.3 fold |
| K SCN | 10 | B3 | 55 | No effect |
| K SCN | 10 | B4 | 1.7 | Increased 1.2 fold |
| 7 | 30 | B3 | 7 | Increased 1.2 fold |
| 7 | 30 | B4 | 6.2 | Increased 2.9 fold |
| 8 | 100 | A | 6 | No effect |
| 8 | 30 | B3 | 20 | No effect |
| 8 | 30 | B4 | 3.5 | Increased 1.5 fold |
| 9 | 30 | B3 | 13 | Decreased 1.4 fold |
| 9 | 30 | B4 | 2.5 | No effect |
| 9 | 100 | B4 | 3 | Increased 4.7 fold |
| 11 | 30 | B3 | 2 | No effect |
| 11 | 30 | B4 | 2.3 | Increased 1.5 fold |
| 11 | 100 | B4 | 3.7 | Increased 1.8 fold |

EXAMPLE 2

Reduction of Autoluminescence Generated by Other Substrates

In addition to looking at the effect of representative compounds on autoluminescence generated from native coelenterazine (Promega Corporation, Madison Wis.) the effect of representative compounds on autoluminescence generated by other substrates was investigated. Coelenterazine analogs N, F, H, HPC, and CP were obtained from Molecular Probes, Eugene Oreg. *Cypridina* luciferin was obtained from NanoLight Technology, Pittsburgh, Pa. Beetle luciferin was obtained from Promega Corporation, Madison Wis. In order to see a more pronounced effect of the compounds, autoluminescence was enhanced as described in Example 1 by the addition of DMSO or detergent (1% Tergitol NP-9/1% Antifoam®) in Matthew's Buffer. Autoluminescence was also enhanced by addition of $H_2O_2$ or by raising the pH of the reaction containing native coelenterazine. Experimental conditions are grouped under Format C, sub-divided as follows:

C1 Alternative Substrates in DMSO
100 μl per well consisting of:
94 μl DMSO
1 μl substrate at 3 mM (30 μM final substrate concentration)

5 µl of compound dissolved in water or water as the control

C2 Alternative Substrates in MB with Detergent

100 µl per well consisting of:

94 µl MB with gelatin in place of BSA and detergent

1 µl substrate at 3 mM (30 µM final substrate concentration)

5 µl of compound dissolved in water or water as the control

C3 MB with BSA, pH 9

100 µl per well consisting of:

90 µl MB (standard composition but at pH 9, 30 µM coelenterazine, no detergent present)

5 µl $H_2O_2$ at 30.7% (1.5% final)

5 µl of compound dissolved in water or water as the control

Reactions were carried out in triplicate by adding each of the components to microtiter plate wells and mixing. The light output was measured immediately using a Dynex MLX Microtiter plate luminometer or a Wallac 1450 MicroBeta Trilux plate luminometer (1 second/well). Results are shown in Table 2.

TABLE 2

| Substrate | mM thiourea Concentration | Format | Fold decrease autoluminescence |
|---|---|---|---|
| native coelenterazine | 25 | C1 | 4.8 |
| coelenterazine analog N | 25 | C1 | 5 |
| coelenterazine analog F | 25 | C1 | 2.6 |
| coelenterazine analog H | 25 | C1 | 1.8 |
| coelenterazine analog HPC | 25 | C1 | 7.2 |
| coelenterazine analog CP | 25 | C1 | 8.7 |
| Cypridina coelenterazine | 25 | C1 | 4.2 |
| Beetle luciferin | 25 | C1 in alkaline environment | 3.8 |
| native coelenterazine | 25 | C2 | 1100 |
| coelenterazine analog N | 25 | C2 | 950 |
| coelenterazine analog F | 25 | C2 | 770 |
| coelenterazine analog H | 25 | C2 | 720 |
| coelenterazine analog HPC | 25 | C2 | 910 |
| coelenterazine analog CP | 25 | C2 | 900 |
| Cypridina coelenterazine | 25 | C2 | 310 |
| native coelenterazine | 50 | C3 | 48 |

EXAMPLE 3

Reduction of Luminescence Generated by Chemiluminescent Substrates CDP-Star® and Luminol The effect of a representative compound on chemiluminescent reactions containing CDP-Star® or Luminol was measured. CDP-Star® is a stabilized 1,2-dioxetane chemiluminescent enzyme substrate, a high energy luminogenic molecule, used in the detection of alkaline phosphatase and alkaline phosphatase conjugates in solution and in membrane-based assays. CDP-Star® was obtained from Tropix PE Biosystems, Bedford, Mass. CDP-Star® substrate produces a light signal when it is activated by alkaline phosphatase. Alkaline phosphatase dephosphorylates the substrate, yielding an anion that accumulates due to its long half-life. Since the ultimate light production involves decomposition of the anion, a delay precedes constant signal output, resulting in a glow of light that lasts for hours to days. Luminol (5-Amino-2,3-didydro-1,4-phthalazinedione) was obtained from Sigma, St. Louis, Mo. Luminol is a widely used chemiluminescent reagent, that luminesces upon oxidation. Experimental conditions are grouped under Format D, sub-divided as follows:

D1 CDP-Star®+Thiourea in Water

In microtiter plate wells, various amounts of CDP-Star® reagent as listed below were mixed with the representative compound in water (or water alone as control) and measured in a luminometer as previously described (1 second/well).

50% 50 µl CDP-Star®+50 µl 0.5 M thiourea (250 mM CDP-Star® final conc.)

75% 75 µl CDP-Star®+25 µl 0.5 M thiourea (125 mM CDP-Star® final conc.)

95% 95 µl CDP-Star®+5 µl 0.5 M thiourea (25 mM CDP-Star® final conc.)

D2 CDP-Star® Undiluted

Thiourea was dissolved directly into CDP-Star® reagent at a concentration of 10 mM. Control reactions contained CDP-Star® reagent alone (100 µl per well) and light output was measured on a MLX Microtiter plate luminometer or a Wallac 1450 MicroBeta Trilux plate luminometer (1 second read per well).

Parallel wells containing 0.28 pg alkaline phosphatase were also measured to monitor the CDP-Star's integrity and activity in these conditions.

D3 Luminol

When a solution containing Luminol comes in contact with $H_2O_2$, a chemiluminescent reaction occurs. The effect of thiourea on this Luminol reaction was measured on the following reactions assembled in a microtiter plate:

50 µl Luminol solution[6]

45 µl 0.0015% or 0.00015% $H_2O_2$

5 µl 0.5 M thiourea (25 mM final conc.) or water as control

[6] Luminol solution per 100 ml:

0.4 gm sodium carbonate 0.02 gm luminol 2.4 gm sodium bicarbonate 0.05 gm ammonium carbonate 0.04 gm copper (II) sulfate pentahydrate distilled water to 100 ml pH 9.0

The resulting luminescence was immediately measured using a Dynex MLX Microtiterplate luminometer or a Wallac 1450 MicroBeta Trilux plate luminometer (1 sec read per well). The results are listed in Table 3. The data demonstrate that thiourea acts on both CDP-Star® and Luminol chemiluminescence reactions to decrease autoluminescence.

TABLE 3

| Substrate | mM thiourea conc. (final) | Format | Fold decrease luminescence |
|---|---|---|---|
| CDP-Star | 250 | D1 50% | 40 |
| CDP-Star | 125 | D1 75% | 6 |
| CDP-Star | 25 | D1 95% | 2 |
| CDP-Star | 10 | D2 | 1.6* |
| Luminol | 25 | D3 0.0015% H2O2 | 150,000 |
| Luminol | 25 | D3 0.00015% H2O2 | 3840 |

*A parallel reaction was conducted containing Alkaline Phospatase (AP) to monitor the effect of thiourea on CDP-Star ® stability. The reaction containing AP also decreased the luminescence output but at a lesser magnitude than that of the CDP-Star ® alone. The AP reaction decreased 1.4 fold in the presence of thiourea.

EXAMPLE 4

Effect of pH on Coelenterazine Derived Autoluminescence

The following experiment was performed to determine the ability of thiourea to reduce autoluminescence at various pH values.

Matthew's buffer was made at a 2× concentration (standard formulation as described in Example 1) and divided in several aliquots. Aliquots were adjusted from pH 4 to pH 9 in one pH unit increments. For each pH, versions of the buffer were made with or without 1% Tergitol NP-9/1% antifoaming agent (referred to as "detergent") and with or without 3 mM thiourea. Coelenterazine was added to a concentration of 180 mM for the version with detergent, and to a concentration of 60 mM for the version without detergent. The buffers were then brought to a final 1× concentration with water.

A 150 μl aliquot of each reaction was dispensed in triplicate into microtiter plate wells and the plate was incubated at 22° C. After 5 minutes the luminescence was measured using a plate luminometer as previously described (1 sec per well) and the results are shown in the following tables:

| Matthew's Buffer with Detergent | | | | | | |
|---|---|---|---|---|---|---|
| | pH 4 | pH 5 | pH 6 | pH 7 | pH 8 | pH 9 |
| Luminescence without thiourea (relative light units) | 1.45 | 3.78 | 56 | 137.5 | 224.7 | 361.1 |
| Luminescence with 3 mM thiourea (relative light units) | .0375 | .04625 | .21 | .71 | 1.62 | 1.77 |
| Fold Reduction | 38.3 | 81.7 | 266.8 | 193.6 | 138.4 | 204.4 |

| Matthew's Buffer without Detergent | | | | | | |
|---|---|---|---|---|---|---|
| | pH 4 | pH 5 | pH 6 | pH 7 | pH 8 | pH 9 |
| Luminescence without thiourea (relative light units) | 0.0925 | 0.2 | 0.78 | 3.63 | 39.62 | 56.36 |
| Luminescence with 3 mM thiourea (relative light units) | 0.025 | 0.024 | 0.063 | 0.259 | 1.52 | 1.785 |
| Fold Reduction | 3.7 | 8.4 | 12.4 | 14 | 26.1 | 31.6 |

These results demonstrate that increasing the pH of the buffer increases coelenterazine auto luminescence. The addition of 3 mm thiourea effectively decreases autoluminescence even at high pHs.

EXAMPLE 5

Reduction of Auto Luminescence in Whole Cell Assay

To determine the effect of organic compounds on cell viability and to determine the ability of such compounds to reduce autoluminescence in the presence of living cells, the following experiment was performed. Human embryonic kidney cells (293, ATCC, Rockville, Md.) were used to generate a cell line that stably expresses the firefly luciferase (Luc+) gene. This stable cell line was made using the pCl-neo vector (Promega Corporation, Madison Wis., USA) and inserting the Luc+ gene between the Xba I and Sal I sites. The stable cell line was prepared using standard methods and the transformed cells were grown in wells of a microtiter plate in the presence of DMEM medium containing 10% FBS and 0.15 mg/ml G418. For experimental purposes, duplicate plates of cells were prepared using 96 well microtiter plates. One plate was used to examine viability, and the other plate was used to examine the effect on autoluminescence.

To examine the effect of the organic compounds in cell viability, the media was removed from the cells and replaced with media containing the substrate for firefly luciferase, beetle luciferin, and the organic compounds at various concentrations. Passive diffusion of luciferin across the cell membrane together with the ATP oxygen and luciferase enzyme already contained within the cell, results in light production. Whereas, in compromised or damaged cells, intracellular ATP concentration is rapidly depleted, decreasing the firefly luminescence. The level of luminescence was compared to controls containing only luciferin to identify the effect of the compounds, if any, on light output as an indicator of cell viability.

To determine the ability of the organic compounds to reduce autoluminescence, the media was removed from the cells and replaced with media containing the compounds at various concentrations and coelenterazine. Since there is no Renilla luciferase enzyme being expressed in these cells, the only luminescence observed is autoluminescence. The level of autoluminescence was compared to controls containing only coelenterazine to identify the effect of the compounds on reducing autoluminescence.

Half of the microtiter plate contained no cells. To these wells, the same reagents were added as to the cell counterpart to measure cell-independent luminescence (i.e. background luminescence). The reagents (media with luciferin or coelenterazine, with or without compounds at various concentrations) were prepared as follows:

a) Reagent to Examine Firefly Luminescence (Cell Viability)

Luciferin substrate available from Promega Corporation, Madison Wis., USA was initially prepared in 10 mM sodium phosphate buffer, pH 7.4 as a 100 mM stock. This luciferin stock was used to make DMEM solution containing a final concentration of 2 mM luciferin.

Thiourea and 1-allyl-3-(2-hydroxyethyl)-2-thiourea were dissolved directly in this solution (DMEM/luciferin) to a final concentration of 30 mM. These were subsequently diluted to contain final compound concentrations of 10 mM and 1 mM.

Another compound 6-aza-thio-thymidine was dissolved in DMSO as a 750 mM stock. The 6-aza-thio-thymidine was subsequently added to the DMEM/luciferin reagent at a final concentration of 30 mM, 10 mM, and 1 mM, while maintaining a final DMSO concentration of 4%. A DMEM/luciferin reagent was used as the control with which to compare the effect of the compound and was also made to contain a final DMSO concentration of 4%.

Since it is believed that DMSO may help organic molecules permeat cell membranes, an additional control was included that consisted of thiourea (10 mM) reconstituted in DMSO (4%).

b) Reagent to Examine Reduction in Autoluminescence

Coelenterazine substrate was initially dissolved in Stop & Glo® Reagent Solvent (both available from Promega Corporation, Madison Wis., USA) as a 30 mM stock. This coelenterazine stock was used to make DMEM media containing 0.6 mM coelenterazine as the final concentration. DMEM/coelenterazine reagents were made in a similar fashion as the DMEM/luciferin reagents described in a).

The cell culture medium was removed from the cells and replaced with medium containing substrate (+/−compound) and luminescence was measured immediately. All luminescent values obtained from wells containing cells were background subtracted using the corresponding luminescent values from those wells that did not contain cells. Fold reduction in autoluminescence was calculated by dividing the background-subtracted autoluminescence in minus compound controls by the background-subtracted autoluminescence containing the compounds.

Results for representative compounds are shown in the following

TABLE

| Compound | Concentration | Additives to Media? | Effects on firefly luminescence | Fold Decrease in Autoluminescence |
| --- | --- | --- | --- | --- |
| Thiourea | 30 mM | No | Yes, decreases | 40 |
| Thiourea | 10 mM | No | No | 16 |
| Thiourea | 1 mM | No | No | 3.4 |
| Thiourea | 10 mM | 4% DMSO | No | 12 |
| 1-Allyl-3-(2-hydroxyethyl)-2-thiourea | 30 mM | No | Yes, decreases | 35 |
| 1-Allyl-3-(2-hydroxyethyl)-2-thiourea | 10 mM | No | Yes, decreases | 12 |
| 1-Allyl-3-(2-hydroxyethyl)-2-thiourea | 1 mM | No | No | 3.5 |
| 6-aza-thio-thymidine | 30 mM | 4% DMSO | Yes, decreases | 525 |
| 6-aza-thio-thymidine | 10 mM | 4% DMSO | No | 23 |
| 6-aza-thio-thymidine | 1 mM | 4% DMSO | No | 3 |

These results demonstrate that these compounds can be used to reduce autoluminescence in luminescent assays employing whole cells without significantly decreasing cell viability.

All publications, patents, and patent documents are incorporated by reference herein, as though individually incorporated by reference. The invention has been described with reference to various specific and preferred embodiments and techniques. However, it should be understood that many variations and modifications can be made while remaining within the spirit and scope of the invention.

What is claimed is:

1. A method for increasing the sensitivity of a bio-luminescent assay comprising carrying out the assay in the presence of an organic compound that reduces luminescence that is not dependent on the presence of an analyte by at least about 10 fold, and that reduces luminescence that is dependent on the presence of an analyte by less than about 7 fold, wherein the organic compound has at least one carbon-sulfur single bond (C—S), carbon-sulfur double bond (C=S), or carbon-selenium double bond (C=Se).

2. The method of claim 1 wherein the luminescence that is dependent on the presence of an analyte is reduced by less than about 5 fold.

3. The method of claim 1 wherein the luminescence that is dependent on the presence of an analyte is reduced by less than about 2 fold, remains the same, or is increased.

4. The method of claim 1 wherein the luminescence that is dependent on the presence of an analyte is maintained or increases.

5. The method of claim 1 wherein the luminescence that is not dependent on the presence of an analyte is chemiluminescence that does not result from a bio-luminescent reaction.

6. The method of claim 1 wherein the luminescence that is dependent on the presence of an analyte comprises luminescence generated within a living cell.

7. The method of claim 1 wherein luminescence that is not dependent on the presence of an analyte comprises luminescence generated by a chemical reaction of coelenterazine or a functional analog thereof.

8. A method for increasing the sensitivity of a luminescent assay comprising carrying out the assay in the presence of an organic compound that reduces luminescence generated by luminogenic molecules not bound to an enzyme by at least about 10 fold, and that reduces the luminescence generated by luminogenic molecules bound to an enzyme by less than about 7 fold, wherein the organic compound has at least one carbon-sulfur single bond (C—S), carbon-sulfur double bond (C=S), or carbon-selenium double bond (C=Se).

9. The method of claim 8 wherein the luminescence generated by luminogenic molecules bound to an enzyme is reduced by less than about 5 fold.

10. The method of claim 8 wherein the luminescence generated by luminogenic molecules bound to an enzyme is reduced by less than about 2 fold, remains the same, or is increased.

11. The method of claim 8 wherein the luminescence generated by luminogenic molecules bound to an enzyme is maintained or increases.

12. The method of claim 8 wherein the luminescence generated by luminogenic molecules bound to an enzyme comprises luminescence generated within a living cell.

13. The method of claim 8 wherein the luminescence generated by luminogenic molecules not bound to an enzyme comprises luminescence generated by a chemical reaction of coelenterazine or a functional analog thereof.

14. A method for increasing the sensitivity of a bioluminescent assay comprising carrying out the assay in the presence of an organic compound that reduces autoluminescence by at least about 10 fold, and that reduces luminescence that is dependent on the presence of an analyte by less than about 7 fold, wherein the organic compound has at least one carbon-sulfur single bond (C—S), carbon-sulfur double bond (C=S), or carbon-selenium double bond (C=Se).

15. The method of any one of claims 1–14 wherein the luminescent assay employs a luciferase, aequorin, or obelin enzyme.

16. The method of any one of claims 1–14 wherein the luminescent assay employs firefly luciferase.

17. The method of any one of claims 1–14 wherein the luminescent assay employs *Renilla* luciferase.

18. The method of any one of claims 1–14 wherein the luminescent assay employs *Cypridina* luciferase.

19. The method of any one of claims 1–14 wherein the organic compound is present in a concentration of at least 0.1 µM.

20. The method of any one of claims 1–14 wherein the organic compound is present in a concentration of at least 0.1 mM.

21. The method of any one of claims 1–14 wherein the organic compound is present in a concentration of from about 0.1 µM to about 500 mM.

22. The method of any one of claims 1–14 wherein the organic compound is present in a concentration of from about 100 µM to about 100 mM.

23. The method of any one of claims 1–14 wherein the organic compound is present in a concentration of from about 10 mM to about 100 mM.

24. The method of any one of claims 1–14 wherein the assay is performed in the presence of whole cells.

25. The method of any one of claims 1–14 wherein the assay is carried out in a solvent comprising at least about 10% water by weight.

26. The method of any one of claims 1–14 wherein the assay is carried out in a solvent comprising at least about 25% water by weight.

27. The method of claim 14 wherein the luminescence that is dependent on the presence of an analyte is reduced by less than about 5 fold.

28. The method of claim 14 wherein the luminescence that is dependent on the presence of an analyte is reduced by less than about 2 fold, remains the same, or is increased.

29. The method of claim 14 wherein the luminescence that is dependent on the presence of an analyte is maintained or increases.

30. The method of claim 14 wherein the luminescence that is dependent on the presence of an analyte comprises luminescence generated within a living cell.

31. The method of claim 14 wherein the auto luminescence comprises luminescence generated by a chemical reaction of coelenterazine or a functional analog thereof.

32. An assay kit comprising packaging material containing 1) a luminogenic substrate of a luminescent enzyme, or a luminogenic enzyme; and 2) an organic compound in an amount for reducing luminescence that is not dependent on the presence of an analyte by at least about 10 fold, and for reducing luminescence that is dependent on the presence of an analyte by less than about 7 fold, wherein the organic compound has at least one carbon-sulfur single bond (C—S), carbon-sulfur double bond (C=S), or carbon-selenium double bond (C=Se).

33. The assay kit of claim 32 wherein the luminescence that is dependent on the presence of an analyte is maintained or increases.

34. The assay kit of claim 32 wherein the luminescence that is dependent on the presence of an analyte comprises luminescence generated within a living cell.

35. The kit of claim 32, further comprising instructions for use of the organic compound in an amount for reducing luminescence that is not dependent on the presence of an analyte by at least about 10 fold, and for reducing luminescence that is dependent on the presence of an analyte by less than about 7 fold.

36. An assay kit comprising packaging material containing 1) a luminogenic substrate of a luminescent enzyme, or a luminogenic enzyme; and 2) an organic compound for reducing luminescence generated by luminogenic molecules not bound to an enzyme by at least about 10 fold, and for reducing luminescence generated by luminogenic molecules bound to an enzyme by less than about 7 fold, wherein the organic compound has at least one carbon-sulfur single bond (C—S), carbon-sulfur double bond (C=S), or carbon-selenium double bond (C=Se).

37. The assay kit of claim 36 wherein the luminescence generated by luminogenic molecules bound to an enzyme is maintained or increases.

38. The assay kit of claim 36 wherein the luminescence generated by luminogenic molecules bound to an enzyme comprises luminescence generated within a living cell.

39. The kit of claim 36, further comprising instructions for use of the organic compound in an amount for reducing luminescence generated by luminogenic molecules not bound to an enzyme by at least about 10 fold, and for reducing luminescence generated by luminogenic molecules bound to an enzyme by less than about 7 fold.

40. An assay kit comprising 1) a luminogenic substrate of a luminescent enzyme, or a luminogenic enzyme; and 2) an organic compound in an amount for reducing autoluminescence by at least about 10 fold, and for reducing luminescence that is dependent on the presence of an analyte by less than about 7 fold, wherein the organic compound has at least one carbon-sulfur single bond (C—S), carbon-sulfur double bond (C=S), or carbon-selenium double bond (C=Se).

41. The kit of any one of claims 32–40 wherein the enzyme substrate and the compound are each contained in a separate container.

42. The kit of any one of claims 32–40 wherein the enzyme substrate and the compound are contained in a single container.

43. The kit of any one of claims 32–40 further comprising a buffer solution suitable for use in a luminescent assay.

44. The kit of claim 43 wherein the enzyme substrate and the buffer solution are contained in a single container.

45. The kit of claim 43 wherein the compound and the buffer solution are contained in a single container.

46. The kit of any one of claims 32–40 further comprising a substrate for a second luminescent enzyme.

47. The kit of any one of claims 32–40 further comprising a quenching agent for a luminescent enzyme reaction.

48. The kit of any one of claims 32–40 wherein the substrate is a substrate for firefly luciferase or a substrate for *Renilla* luciferase.

49. The kit of any one of claims 32–40 further comprising ATP.

50. The kit of any one of claims 32–40 that comprises both a luminogenic substrate of a luminescent enzyme, and a luminogenic enzyme.

51. The assay kit of claim 40 wherein the luminescence that is dependent on the presence of an analyte is maintained or increases.

52. The assay kit of claim 40 wherein the luminescence that is dependent on the presence of an analyte comprises luminescence generated within a living cell.

53. The kit of claim 40, further comprising instructions for use of the organic compound in an amount for reducing autoluminescence by at least about 10 fold, and for reducing luminescence that is dependent on the presence of an analyte by less than about 7 fold.

54. A method for increasing the sensitivity of a bio-luminescent assay comprising carrying out the assay in the presence of an organic compound that reduces the luminescence that does not result from a bio-luminescent reaction by at least about 10 fold, and that reduces luminescence that does result from a bio-luminescent reaction by less than about 7 fold, wherein the organic compound has at least one carbon-sulfur single bond (C—S), carbon-sulfur double bond (C=S), or carbon-selenium double bond (C=Se).

55. The method of claim 54 wherein the luminescence that results from a bio-luminescent reaction is maintained or increases.

56. The method of claim 54 wherein the luminescence that does not result from a bio-luminescent reaction comprises luminescence generated within a living cell.

57. The method of claim 54 wherein the luminescence that does not result from a bio-luminescent reaction comprises luminescence generated by a chemical reaction of coelenterazine or a functional analog thereof.

58. The method of any one of claims 1, 8, 14, and 54 wherein the organic compound comprises a sulfur atom or a selenium atom.

59. The method of any one of claims 1, 8, 14, and 54 wherein the organic compound contains a carbon-sulfur double bond (C=S).

60. The method of any one of claims 1, 8, 14, and 54 wherein the organic compound contains a carbon-selenium double bond (C=Se).

61. The method of any one of claims 1, 8, 14, and 54 wherein the organic compound is a compound of formula (I):

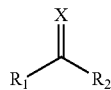

(I)

wherein X is S or Se; $R_1$ and $R_2$ are each independently hydrogen, $(C_1-C_{20})$alkyl, $(C_3-C_8)$cycloalkyl, $(C_1-C_{20})$alkoxy, $(C_2-C_{20})$alkenyl, $(C_2-C_{20})$alkynyl, aryl, heteroaryl, or $NR_aR_b$; or $R_1$ and $R_2$ together with the carbon to which they are attached form a 5, 6, 7, or 8 membered saturated or unsaturated ring comprising carbon and optionally comprising 1, 2, or 3 heteroatoms selected from oxy (—O—), thio (—S—), or nitrogen (—$NR_c$—), wherein said ring is optionally substituted with 1, 2, or 3 halo, hydroxy, oxo, thioxo, carboxy, $(C_1-C_{20})$alkyl, $(C_3-C_8)$cycloalkyl, $(C_1-C_{20})$alkoxy, $(C_1-C_{20})$alkanoyl, $(C_1-C_{20})$alkoxycarbonyl, $(C_2-C_{20})$alkenyl, $(C_2-C_{20})$alkynyl, aryl, or heteroaryl; and $R_a$, $R_b$ and $R_c$ are each independently hydrogen, $(C_1-C_{20})$alkyl, $(C_3-C_8)$cycloalkyl, $(C_2-C_{20})$alkenyl, $(C_1-C_{20})$alkanoyl, $(C_1-C_{20})$alkoxycarbonyl, $(C_2-C_{20})$alkynyl, aryl, heteroaryl; wherein any $(C_1-C_{20})$alkyl, $(C_3-C_8)$cycloalkyl, $(C_1-C_{20})$alkoxy, $(C_2-C_{20})$alkenyl $(C_1-C_{20})$alkanoyl, $(C_1-C_{20})$alkoxycarbonyl, or $(C_2-C_{20})$alkynyl of $R_1$, $R_2$, $R_a$, $R_b$, and $R_c$ is optionally substituted with one or more halo, hydroxy, mercapto, oxo, thioxo, carboxy, $(C_1-C_{20})$alkanoyl, $(C_1-C_{20})$alkoxycarbonyl, aryl, or heteroaryl; and wherein any aryl or heteroaryl is optionally substituted with one or more halo, hydroxy, mercapto, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

62. The method of any one of claims 1, 8, 14, and 54 wherein the organic compound is a compound of formula $R_3SH$ wherein $R_3$ is $(C_1-C_{20})$alkyl, $(C_3-C_8)$cycloalkyl, $(C_2-C_{20})$alkenyl, $(C_2-C_{20})$alkynyl, aryl, or heteroaryl; wherein any $(C_1-C_{20})$alkyl, $(C_3-C_8)$cycloalkyl, $(C_2-C_{20})$alkenyl, or $(C_2-C_{20})$alkynyl of $R_3$ is optionally substituted with one or more halo, hydroxy, mercapto oxo, thioxo, carboxy, $(C_1-C_{20})$alkanoyl, $(C_1-C_{20})$alkoxycarbonyl, aryl, heteroaryl, or $NR_dR_e$; wherein $R_d$ and $R_e$ are each independently hydrogen, $(C_1-C_{20})$alkyl, $(C_3-C_8)$cycloalkyl, $(C_2-C_{20})$alkenyl, $(C_2-C_{20})$alkynyl, $(C_1-C_{20})$alkanoyl, $(C_1-C_{20})$alkoxycarbonyl, aryl, or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

63. The method of any one of claims 1, 8, 14, and 54 wherein the organic compound is a compound of formula $R_4NCS$ wherein: $R_4$ is $(C_1-C_{20})$alkyl, $(C_3-C_8)$cycloalkyl, $(C_2-C_{20})$alkenyl, $(C_2-C_{20})$alkynyl, aryl, or heteroaryl; wherein any $(C_1-C_{20})$alkyl, $(C_3-C_8)$cycloalkyl, $(C_2-C_{20})$alkenyl, or $(C_2-C_{20})$alkynyl of $R_4$ is optionally substituted with one or more halo, hydroxy, mercapto, oxo, thioxo, carboxy, $(C_1-C_{20})$alkanoyl, $(C_1-C_{20})$alkoxycarbonyl, aryl, heteroaryl, or $NR_fR_g$; wherein $R_f$ and $R_g$ are each independently hydrogen, $(C_1-C_{20})$alkyl, $(C_3-C_8)$cycloalkyl, $(C_2-C_{20})$alkenyl, $(C_2-C_{20})$alkynyl, $(C_1-C_{20})$alkanoyl, $(C_1-C_{20})$alkoxycarbonyl, aryl, or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

64. The method of any one of claims 1, 8, 14, and 54 wherein the organic compound is a compound of formula $R_5$—X—$R_6$ wherein:

X is —S— or —Se—;

$R_5$ is $(C_1-C_{20})$alkyl, $(C_3-C_8)$cycloalkyl, $(C_2-C_{20})$alkenyl, $(C_2-C_{20})$alkynyl, aryl, or heteroaryl; and $R_6$ is hydrogen, $(C_1-C_{20})$alkyl, $(C_3-C_8)$cycloalkyl, $(C_2-C_{20})$alkenyl, $(C_2-C_{20})$alkynyl, aryl, or heteroaryl;

or $R_5$ and $R_6$ together with X form a heteroaryl;

wherein any $(C_1-C_{20})$alkyl, $(C_3-C_8)$cycloalkyl, $(C_2-C_{20})$alkenyl, or $(C_2-C_{20})$alkynyl of $R_5$ or $R_6$ is optionally substituted with one or more halo, hydroxy, mercapto, oxo, thioxo, carboxy, $(C_1-C_{20})$alkanoyl, $(C_1-C_{20})$alkoxycarbonyl, aryl, heteroaryl, or $NR_kR_m$;

wherein $R_k$ and $R_m$ are each independently hydrogen, $(C_1-C_{20})$alkyl, $(C_3-C_8)$cycloalkyl, $(C_2-C_{20})$alkenyl, $(C_2-C_{20})$alkynyl, $(C_1-C_{20})$alkanoyl, $(C_1-C_{20})$alkoxycarbonyl, aryl, or heteroaryl; and wherein any aryl or heteroaryl is optionally substituted with one or more halo, mercapto, hydroxy, oxo, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

65. The method of any one of claims 1, 8, 14, and 54 wherein the organic compound is a compound of any one of formulae 1–11

1
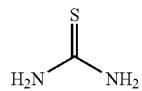

2
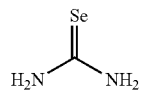

3
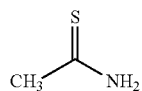

4
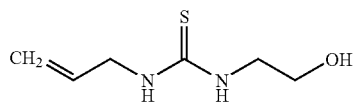

5
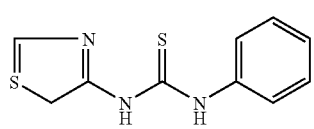

6
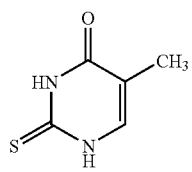

7
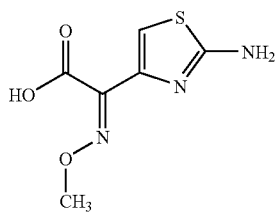

8
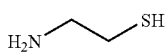

9
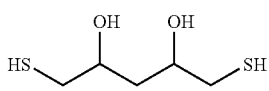

10
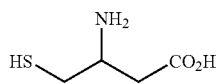

-continued

11
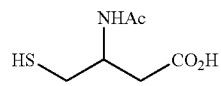

66. The method of any one of claims 1, 8, 14, and 54 wherein the organic compound is a compound of formulae 1, 8, 15, or 17 as shown

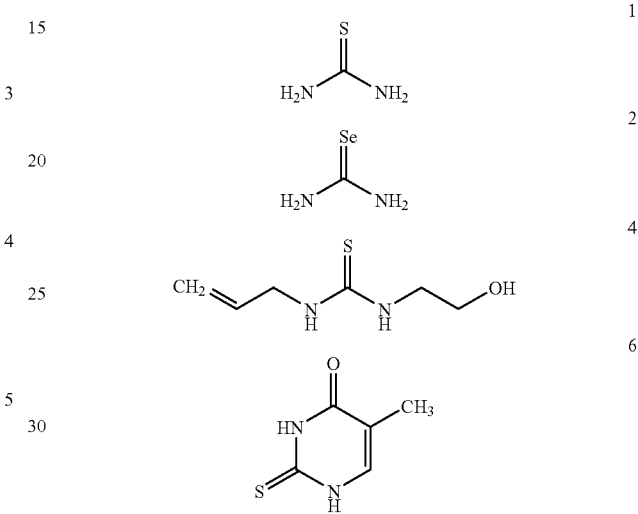

67. The method of any one of claim 1, 8, 14, or 54, wherein the organic compound is not a polypeptide or protein comprising one or more mercapto (C—SH) groups.

68. The method of any one of claim 1, 8, 14, or 54, wherein the organic compound does not comprise one or more mercapto (C—SH) groups.

69. An assay kit comprising packaging material containing 1) a luminogenic substrate of an enzyme, or a luminogenic enzyme; and 2) an organic compound for reducing luminescence that does not result from a bio-luminescent reaction by at least about 10 fold, and that reduces luminescence does result from a bio-luminescent reaction by less than about 7 fold, wherein the organic compound has at least one carbon-sulfur single bond (C—S), carbon-sulfur double bond (C=S), or carbon-selenium double bond (C=Se).

70. The assay kit of claim 69 wherein the luminescence that results from a bio-luminescent reaction is maintained or increases.

71. The assay kit of claim 69 wherein the luminescence that does not result from a bio-luminescent reaction comprises luminescence generated within a living cell.

72. The kit of claim 69, further comprising instructions for use of the organic compound in an amount for reducing luminescence that does not result from a bio-luminescent reaction by at least about 10 fold, and for reducing luminescence that does result from a bio-luminescent reaction by less than about 7 fold.

73. The kit of any one of claims 32, 36, 40, and 69 wherein the organic compound comprises a sulfur atom or a selenium atom.

74. The kit of any one of claims 32, 36, 40, and 69 wherein the organic compound contains a carbon-sulfur double bond (C=S).

75. The kit of any one of claims 32, 36, 40, and 69 wherein the organic compound contains a carbon-selenium double bond (C=Se).

76. The kit of any one of claims 32, 36, 40, and 69 wherein the organic compound is a compound of formula (I):

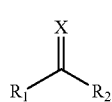

wherein X is S or Se; $R_1$ and $R_2$ are each independently hydrogen, $(C_1-C_{20})$alkyl, $(C_3-C_8)$cycloalkyl, $(C_1-C_{20})$alkoxy, $(C_2-C_{20})$alkenyl, $(C_2-C_{20})$alkynyl, aryl, heteroaryl, or $NR_aR_b$; or $R_1$ and $R_2$ together with the carbon to which they are attached form a 5, 6, 7, or 8 membered saturated or unsaturated ring comprising carbon and optionally comprising 1, 2, or 3 heteroatoms selected from oxy (—O—), thio (—S—), or nitrogen (—$NR_c$—), wherein said ring is optionally substituted with 1, 2, or 3 halo, hydroxy, oxo, thioxo, carboxy, $(C_1-C_{20})$alkyl, $(C_3-C_8)$cycloalkyl, $(C_1-C_{20})$alkoxy, $(C_1-C_{20})$alkanoyl, $(C_1-C_{20})$alkoxycarbonyl, $(C_2-C_{20})$alkenyl, $(C_2-C_{20})$alkynyl, aryl, or heteroaryl; and $R_a$, $R_b$ and $R_c$ are each independently hydrogen, $(C_1-C_{20})$alkyl, $(C_3-C_8)$cycloalkyl, $(C_2-C_{20})$alkenyl, $(C_1-C_{20})$alkanoyl, $(C_1-C_{20})$alkoxycarbonyl, $(C_2-C_{20})$alkynyl, aryl, heteroaryl; wherein any $(C_1-C_{20})$alkyl, $(C_3-C_8)$cycloalkyl, $(C_1-C_{20})$alkoxy, $(C_2-C_{20})$alkenyl $(C_1-C_{20})$alkanoyl, $(C_1-C_{20})$alkoxycarbonyl, or $(C_2-C_{20})$alkynyl of $R_1$, $R_2$, $R_a$, $R_b$, and $R_c$ is optionally substituted with one or more halo, hydroxy, mercapto, oxo, thioxo, carboxy, $(C_1-C_{20})$alkanoyl, $(C_1-C_{20})$alkoxycarbonyl, aryl, or heteroaryl; and wherein any aryl or heteroaryl is optionally substituted with one or more halo, hydroxy, mercapto, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

77. The kit of any one of claims 32, 36, 40, and 69 wherein the organic compound is a compound of formula $R_3SH$ wherein $R_3$ is $(C_1-C_{20})$alkyl, $(C_3-C_8)$cycloalkyl, $(C_2-C_{20})$alkenyl, $(C_2-C_{20})$alkynyl, aryl, or heteroaryl; wherein any $(C_1-C_{20})$alkyl, $(C_3-C_8)$cycloalkyl, $(C_2-C_{20})$alkenyl, or $(C_2-C_{20})$alkynyl of $R_3$ is optionally substituted with one or more halo, hydroxy, mercapto, oxo, thioxo, carboxy, $(C_1-C_{20})$alkanoyl, $(C_1-C_{20})$alkoxycarbonyl, aryl, heteroaryl, or $NR_dR_e$; wherein $R_d$ and $R_e$ are each independently hydrogen, $(C_1-C_{20})$alkyl, $(C_3-C_8)$cycloalkyl, $(C_2-C_{20})$alkenyl, $(C_2-C_{20})$alkynyl, $(C_1-C_{20})$alkanoyl, $(C_1-C_{20})$alkoxycarbonyl, aryl, or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

78. The kit of any one of claims 32, 36, 40, and 69 wherein the organic compound is a compound of formula $R_4NCS$ wherein: $R_4$ is $(C_1-C_{20})$alkyl, $(C_3-C_8)$cycloalkyl, $(C_2-C_{20})$alkenyl, $(C_2-C_{20})$alkynyl, aryl, or heteroaryl; wherein any $(C_1-C_{20})$alkyl, $(C_3-C_8)$cycloalkyl, $(C_2-C_{20})$alkenyl, or $(C_2-C_{20})$alkynyl of $R_3$ is optionally substituted with one or more halo, hydroxy, mercapto oxo, thioxo, carboxy, $(C_1-C_{20})$alkanoyl, $(C_1-C_{20})$alkoxycarbonyl, aryl, heteroaryl, or $NR_fR_g$; wherein $R_f$ and $R_g$ are each independently hydrogen, $(C_1-C_{20})$alkyl, $(C_3-C_8)$cycloalkyl, $(C_2-C_{20})$alkenyl, $(C_2-C_{20})$alkynyl, $(C_1-C_{20})$alkanoyl, $(C_1-C_{20})$alkoxycarbonyl aryl, or heteroaryl; and wherein any aryl or heteroaryl is optionally substituted with one or more (1, 2, 3, or 4) halo, mercapto, hydroxy, oxo, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

79. The kit of any one of claims 32, 36, 40, and 69 wherein the organic compound is a compound of formula $R_5$—X—$R_6$ wherein:

X is —S— or —Se—;

$R_5$ is $(C_1-C_{20})$alkyl, $(C_3-C_8)$cycloalkyl, $(C_2-C_{20})$alkenyl, $(C_2-C_{20})$alkynyl, aryl, or heteroaryl; and $R_6$ is hydrogen, $(C_1-C_{20})$alkyl, $(C_3-C_8)$cycloalkyl, $(C_2-C_{20})$alkenyl, $(C_2-C_{20})$alkynyl, aryl, or heteroaryl;

or $R_5$ and $R_6$ together with X form a heteroaryl;

wherein any $(C_1-C_{20})$alkyl, $(C_3-C_8)$cycloalkyl, $(C_2-C_{20})$alkenyl, or $(C_2-C_{20})$alkynyl of $R_5$ or $R_6$ is optionally substituted with one or more halo, hydroxy, mercapto, oxo, thioxo, carboxy, $(C_1-C_{20})$alkanoyl, $(C_1-C_{20})$alkoxycarbonyl, aryl, heteroaryl, or $NR_kR_m$;

wherein $R_k$ and $R_m$ are each independently hydrogen, $(C_1-C_{20})$alkyl, $(C_3-C_8)$cycloalkyl, $(C_2-C_{20})$alkenyl, $(C_2-C_{20})$alkynyl, $(C_1-C_{20})$alkanoyl, $(C_1-C_{20})$alkoxycarbonyl, aryl, or heteroaryl; and wherein any aryl or heteroaryl is optionally substituted with one or more halo, mercapto, hydroxy, oxo, carboxy, cyano, nitro, trifluoromethyl, trifluoromethoxy, $(C_1-C_{20})$alkanoyl, $(C_1-C_{20})$alkanoyloxy, sulfo or $(C_1-C_{20})$alkoxycarbonyl; or a salt thereof.

80. The kit of any one of claims 32, 36, 40, and 69 wherein the organic compound is a compound of any one of formulae 1–11

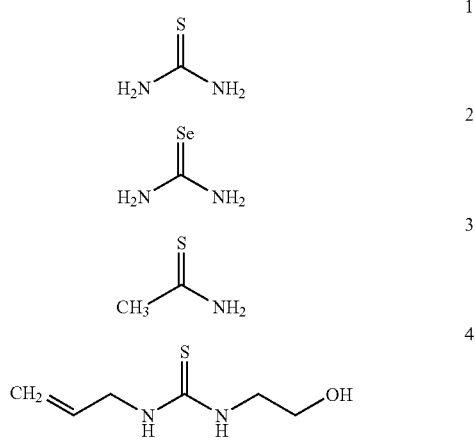

81. The kit of any one of claims 32, 36, 40, and 69 wherein the organic compound is a compound of formula 1, 2, 4, or 6

82. The kit of any one of claim 32, 36, 40, or 69, wherein the organic compound is not a polypeptide or protein comprising one or more mercapto (C—SH) groups.

83. The kit of any one of claim 32, 36, 40, or 69, wherein the organic compound does not comprise one or more mercapto (C—SH) groups.

* * * * *

UNITED STATES PATENT AND TRADEMARK OFFICE
CERTIFICATE OF CORRECTION

PATENT NO.       : 7,118,878 B1                                       Page 1 of 2
APPLICATION NO.  : 09/590884
DATED            : October 10, 2006
INVENTOR(S)      : Hawkins et al.

It is certified that error appears in the above-identified patent and that said Letters Patent is hereby corrected as shown below:

In column 21, lines 55-56, in Claim 31, delete "auto luminescence" and insert -- autoluminescence --, therefor.

In column 21, lines 58-59, in Claim 32, after "comprising" delete "packaging material containing".

In column 23, line 67, in Claim 61, after "$(C_2-C_{20})$alkenyl" insert -- , --.

In column 24, line 16, in Claim 62, after "mercapto" insert -- , --.

In Column 25, lines 64–66, in Claim 65, delete " 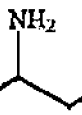 " and insert

-- 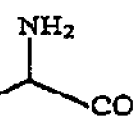 --, therefor.

In column 26, lines 4–6, in Claim 65, delete "  " and insert

-- 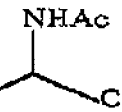 --, therefor.

In column 26, line 11, in Claim 66, after "1," delete "8, 15, or 17" and insert -- 2, 4, or 6 --, therefor.

In column 26, line 11, in Claim 66, after "17" delete "as shown".

In column 27, line 36, in Claim 76, after "$(C_2-C_{20})$alkenyl" insert -- , --.

In column 28, line 5, in Claim 78, after "mercapto" insert -- , --.

In column 28, line 11, in Claim 78, after "$(C_1-C_{20})$alkoxycarbonyl" insert -- , --.

In column 29, lines 39–42, in Claim 80, delete " 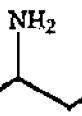 " and insert

-- 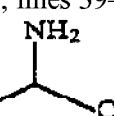 --, therefor.

UNITED STATES PATENT AND TRADEMARK OFFICE
CERTIFICATE OF CORRECTION

PATENT NO. : 7,118,878 B1
APPLICATION NO. : 09/590884
DATED : October 10, 2006
INVENTOR(S) : Hawkins et al.

It is certified that error appears in the above-identified patent and that said Letters Patent is hereby corrected as shown below:

In column 30, lines 3–7, in Claim 80, delete " 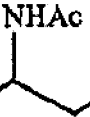 " and insert 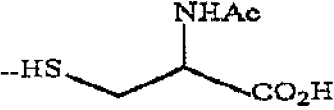 --, therefor.

Signed and Sealed this

Eighteenth Day of September, 2007

JON W. DUDAS
*Director of the United States Patent and Trademark Office*